United States Patent
Evans et al.

(10) Patent No.: US 9,527,787 B2
(45) Date of Patent: Dec. 27, 2016

(54) PROCESS FOR THE PREPARATION OF ALKYLENE CARBONATE AND/OR ALKYLENE GLYCOL

(75) Inventors: Wayne Errol Evans, Richmond, TX (US); Marek Matusz, Houston, TX (US); Eugene Marie Godfried Andre Van Kruchten, Amsterdam (NL); Martin Lysle Hess, Fulshear, TX (US)

(73) Assignee: Shell Oil Company, Houston, TX (US)

( * ) Notice: Subject to any disclaimer, the term of this patent is extended or adjusted under 35 U.S.C. 154(b) by 432 days.

(21) Appl. No.: 13/462,490

(22) Filed: May 2, 2012

(65) Prior Publication Data

US 2012/0213679 A1 Aug. 23, 2012

Related U.S. Application Data

(62) Division of application No. 12/465,492, filed on May 13, 2009, now Pat. No. 8,193,374.

(60) Provisional application No. 61/053,549, filed on May 15, 2008.

(51) Int. Cl.

| | |
|---|---|
| *B01J 19/00* | (2006.01) |
| *C07C 29/12* | (2006.01) |
| *B01D 53/02* | (2006.01) |
| *B01D 53/70* | (2006.01) |
| *C07C 29/10* | (2006.01) |

(52) U.S. Cl.
CPC .............. *C07C 29/12* (2013.01); *B01D 53/02* (2013.01); *B01D 53/70* (2013.01); *C07C 29/106* (2013.01); *B01D 2253/112* (2013.01); *B01D 2255/104* (2013.01); *B01D 2257/2068* (2013.01)

(58) Field of Classification Search
CPC ....... B01J 19/2435; B01J 31/00; C07C 31/202
USPC ............................................ 422/129; 436/37
See application file for complete search history.

(56) References Cited

U.S. PATENT DOCUMENTS

| | | |
|---|---|---|
| 113,534 A | 4/1871 | LaPort |
| 1,153,564 A | 9/1915 | Nichol |
| 1,422,184 A | 7/1922 | Curme, Jr. |
| 1,529,537 A | 4/1923 | Carman et al. |
| 1,741,559 A | 12/1929 | Dawson |

(Continued)

FOREIGN PATENT DOCUMENTS

| | | | |
|---|---|---|---|
| CA | 2003010 | 1/1991 | |
| CN | 1271351 | 9/1998 | ........... C07D 301/10 |

(Continued)

OTHER PUBLICATIONS

Stephen Brunauer et al. "Adsorption of Gases in Multimolecular Layers", pp. 309-316, vol. 60, Feb. 1938.

(Continued)

*Primary Examiner* — Natalia Levkovich

(57) ABSTRACT

The invention provides a reaction system for the production of an alkylene carbonate and/or an alkylene glycol comprising: an epoxidation zone containing an epoxidation catalyst located within an epoxidation reactor; a carboxylation zone containing an iodide-containing carboxylation catalyst located within an alkylene oxide absorber; and one or more purification zones containing a purification absorbent capable of reducing the quantity of iodide-containing impurities in a feed comprising a recycle gas, which purification zones are located upstream from the epoxidation zone; and a process for the production of an alkylene carbonate and/or an alkylene glycol.

14 Claims, 7 Drawing Sheets

(56) References Cited

U.S. PATENT DOCUMENTS

| | | | |
|---|---|---|---|
| 1,851,312 A | 3/1932 | Huff | |
| 2,143,371 A | 1/1939 | Francon | 260/348 |
| 2,378,969 A | 6/1945 | Bailey et al. | 260/677 |
| 2,408,010 A | 9/1946 | Wadley et al. | 260/677 |
| 2,432,423 A | 12/1947 | Hunter | 260/677 |
| 2,491,057 A | 12/1949 | Nevison et al. | 260/348.5 |
| 2,497,296 A | 2/1950 | Chance, Jr. | 260/677 |
| 2,542,520 A | 2/1951 | Hibshman | 183/115 |
| 2,573,341 A | 10/1951 | Kniel | 260/683 |
| 2,588,323 A | 3/1952 | Kniel | 260/677 |
| 2,805,733 A | 9/1957 | Stanton | 183/115 |
| 2,813,920 A | 11/1957 | Cobb, Jr. | 260/683 |
| 2,836,635 A | 5/1958 | Göthel et al. | 260/677 |
| 2,837,587 A | 6/1958 | Hogan et al. | 260/683.15 |
| 2,942,042 A | 6/1960 | Folz | 260/677 |
| 2,953,608 A | 9/1960 | Fernald | 260/667 |
| 2,973,628 A | 3/1961 | Green et al. | 62/24 |
| 3,000,942 A | 9/1961 | Frankel | 260/561 |
| 3,000,988 A | 9/1961 | Karchmer et al. | 260/677 |
| 3,055,183 A | 9/1962 | Kniel | 62/17 |
| 3,106,462 A | 10/1963 | Cottle | 55/20 |
| 3,169,052 A | 2/1965 | Davison | 62/20 |
| 3,324,194 A | 6/1967 | Kanbayashi et al. | 260/677 |
| 3,326,999 A | 6/1967 | Rhodes, Jr. | 260/677 |
| 3,432,573 A | 3/1969 | Keil | 260/683.15 |
| 3,456,029 A | 7/1969 | Morita et al. | 260/677 |
| 3,530,199 A | 9/1970 | Lowrance | 260/683 |
| 3,549,719 A | 12/1970 | Duyverman et al. | 260/677 |
| 3,676,516 A | 7/1972 | Haskell et al. | 260/677 A |
| 3,844,981 A | 10/1974 | Cusumano | 252/471 |
| 4,059,418 A | 11/1977 | Cull | 55/73 |
| 4,085,192 A | 4/1978 | Van Scoy | 423/226 |
| 4,105,588 A | 8/1978 | Balducci et al. | 252/454 |
| 4,182,722 A | 1/1980 | Lyons | 260/348.33 |
| 4,400,559 A | 8/1983 | Bhise | 568/858 |
| 4,508,927 A * | 4/1985 | Bhise et al. | 568/858 |
| 4,620,044 A | 10/1986 | Chang et al. | 568/833 |
| 4,729,889 A | 3/1988 | Flytani-Stephanopoulos et al. | 423/593 |
| 4,766,105 A | 8/1988 | Lauritzen | 502/216 |
| 4,769,047 A | 9/1988 | Dye | 55/26 |
| 4,822,900 A | 4/1989 | Hayden | 549/534 |
| 4,822,926 A | 4/1989 | Dye | 568/867 |
| 4,831,196 A | 5/1989 | Buonicore et al. | 568/867 |
| 4,845,296 A | 7/1989 | Ahmed et al. | 564/477 |
| 4,921,681 A | 5/1990 | Ozero et al. | 422/197 |
| 5,145,824 A | 9/1992 | Buffum et al. | 502/216 |
| 5,157,201 A | 10/1992 | Norris | 585/820 |
| 5,218,135 A | 6/1993 | Buysch et al. | 558/277 |
| 5,262,551 A | 11/1993 | Horrell, Jr. et al. | 549/534 |
| 5,322,615 A | 6/1994 | Holtermann et al. | 208/91 |
| 5,334,742 A | 8/1994 | Schön et al. | 558/274 |
| 5,380,697 A | 1/1995 | Matusz et al. | 502/348 |
| 5,466,837 A | 11/1995 | Ramachandran et al. | 549/533 |
| 5,739,075 A | 4/1998 | Matusz | 502/302 |
| 5,756,779 A | 5/1998 | Stavinoha, Jr. | 549/532 |
| 5,763,691 A | 6/1998 | Kawabe et al. | 568/867 |
| 5,801,115 A | 9/1998 | Albers et al. | 502/342 |
| 5,801,259 A | 9/1998 | Kowaleski | 549/536 |
| 5,990,372 A | 11/1999 | Blankenship et al. | 585/823 |
| 6,040,467 A | 3/2000 | Papavassiliou et al. | 549/534 |
| 6,042,798 A | 3/2000 | Masuda et al. | 423/244.01 |
| 6,080,897 A | 6/2000 | Kawabe | 568/858 |
| 6,124,517 A | 9/2000 | Kaminsky et al. | 585/823 |
| 6,368,998 B1 | 4/2002 | Lockemeyer | 502/347 |
| 6,417,411 B2 | 7/2002 | Kakimoto et al. | 568/867 |
| 6,624,318 B1 | 9/2003 | Müller et al. | 549/529 |
| 6,717,001 B2 | 4/2004 | Evans et al. | 549/536 |
| 6,762,310 B2 | 7/2004 | Neumann et al. | 549/523 |
| 6,765,101 B1 * | 7/2004 | Bhasin et al. | 549/523 |
| 6,939,979 B2 | 9/2005 | Rizkalla et al. | 549/533 |
| 7,132,555 B2 | 11/2006 | Te Raa et al. | 549/534 |
| 2002/0099248 A1 | 7/2002 | Ziaka-Vasileiadou et al. | 585/330 |
| 2003/0017943 A1 | 1/2003 | Shan et al. | 502/243 |
| 2003/0028040 A1 | 2/2003 | Seeba et al. | 549/532 |
| 2003/0098381 A1 | 5/2003 | Mishima et al. | 242/474.8 |
| 2003/0105376 A1 | 6/2003 | Foral et al. | 585/804 |
| 2004/0175316 A1 | 9/2004 | Bos et al. | 423/245.1 |
| 2004/0176653 A1 | 9/2004 | Vorberg et al. | 585/276 |
| 2004/0236124 A1 | 11/2004 | Evans et al. | 549/534 |
| 2004/0267059 A1* | 12/2004 | Powell et al. | 568/867 |
| 2006/0036104 A1 | 2/2006 | Lu et al. | 549/512 |
| 2006/0258529 A1 | 11/2006 | Diefenbacher et al. | 502/321 |
| 2006/0292046 A1 | 12/2006 | Fruchey et al. | 422/197 |
| 2007/0031302 A1 | 2/2007 | Wittrup et al. | 422/168 |
| 2008/0182999 A1 | 7/2008 | Rekers et al. | 549/512 |

FOREIGN PATENT DOCUMENTS

| | | | |
|---|---|---|---|
| CN | 1699359 | 11/2005 | C07D 317/38 |
| DE | 2431034 | 1/1975 | C07D 303/14 |
| DE | 2526153 | 1/1976 | A47L 9/10 |
| DE | 2530091 | 1/1976 | B01D 53/04 |
| DE | 2617649 | 11/1977 | B01D 53/36 |
| DE | 2319532 | 4/1982 | B01D 53/04 |
| DE | 3029188 | 4/1982 | B01D 53/04 |
| DE | 3029197 | 4/1982 | E03F 9/00 |
| DE | 2439234 | 11/1983 | B01D 53/04 |
| DE | 3719138 | 12/1988 | B01D 53/36 |
| EP | 3642 | 8/1979 | C07D 301/10 |
| EP | 0024628 | 3/1981 | C07D 301/32 |
| EP | 0133763 | 7/1984 | C07C 31/20 |
| EP | 266015 | 5/1988 | B01J 23/68 |
| EP | 288912 | 11/1988 | F25J 3/08 |
| EP | 776890 | 1/2001 | C07D 317/38 |
| EP | 1121977 | 1/2001 | B01J 20/18 |
| EP | 1201301 | 5/2002 | B01J 23/58 |
| EP | 0960086 | 10/2002 | C07C 7/04 |
| EP | 1308442 | 5/2003 | C07D 301/10 |
| GB | 580485 | 9/1946 | |
| GB | 846077 | 8/1960 | |
| GB | 887244 | 1/1962 | |
| GB | 1020676 | 2/1966 | |
| GB | 1029878 | 5/1966 | |
| GB | 1090776 | 11/1967 | C07C 11/04 |
| GB | 2107712 | 5/1983 | C07D 317/38 |
| GB | 2206354 | 1/1989 | C07C 7/00 |
| JP | 069591 | 1/1984 | |
| JP | 6212173 | 8/1984 | |
| JP | 59196829 | 11/1984 | |
| JP | 02302301 | 12/1984 | |
| JP | 05508432 | 11/1993 | |
| JP | 2004531542 | 10/2004 | |
| JP | 2006512453 | 4/2006 | |
| WO | 9200261 | 1/1992 | |
| WO | WO9709113 | 3/1997 | B01J 23/06 |
| WO | WO97/22404 | 6/1997 | B01D 53/94 |
| WO | WO9736680 | 10/1997 | B01J 23/68 |
| WO | WO9829366 | 7/1998 | C07C 7/04 |
| WO | WO02053491 | 7/2002 | C01B 3/16 |
| WO | WO02088102 | 11/2002 | C07D 301/04 |
| WO | WO02094435 | 11/2002 | B01J 23/80 |
| WO | WO2004000017 | 5/2004 | B01J 23/58 |
| WO | WO2004039496 | 5/2004 | B01J 23/58 |
| WO | WO2004092148 | 10/2004 | C07D 301/10 |
| WO | WO2006045765 | 5/2006 | B01J 8/04 |
| WO | WO2008144396 | 11/2008 | B01D 53/04 |
| WO | WO2008144409 | 11/2008 | B01J 8/04 |

OTHER PUBLICATIONS

Johann Schlauer, "Absorption, 1. Fundamentals," in "Ullmann's Encyclopedia of Industrial Chemistry," Oct. 15, 2008, John Wiley & Sons, Inc., XP002549130, pp. 1-3.

J. P. Dever, K. F. George, W. C. Hoffman, H. Soo, "Ethylene Oxide", in Kirk-Othmer Encyclopedia of Chemical Technology, Mar. 14, 2004, John Wiley & Sons, Inc., XP002549317, vol. 10, pp. 632-672.

Siegfried Rebsdat et al., "Ethylene Oxide" 2005 Ulmann's Encyclopedia of Industrial Chemistry, Weinhein, VCH Verlag., DE, pp. 1-27, XP002505553.

(56) References Cited

OTHER PUBLICATIONS

K. Otsuka et al., "Electrochemical cells as reactors for selective oxygenation of hydrocarbons at low temperature," Catalysis Today (1998) 41, pp. 311-325.

Naruyoshi Komiya et al., "Aerobic oxidation of alkanes and alkenes in the presence of aldehydes catalyzed by copper salts and copper-crown ether," Journal of Molecular Catalysis A: Chemical (1997) 117, (1-3 Proceedings of 6th Int'l Symposium on the Activation of Dioxygen and Homogeneous Catalytic Oxidation, 1996) pp. 21-37.

J. Rouchaud et al., "Catalysis by Chelates of Transition Elements of the Liquid Phase Oxidation of Propylene," Journal of Catalysis (1970) 19(2) pp. 172-175.

* cited by examiner

PROCESS FOR THE PREPARATION OF ALKYLENE CARBONATE AND/OR ALKYLENE GLYCOL

REFERENCE TO PRIOR APPLICATION

This application is a division of U.S. application Ser. No. 12/465,492 filed May 13, 2009, allowed, which claims the benefit of provisional U.S. Application Ser. No. 61/053,549, filed May 15, 2008, the entire disclosure of which is hereby incorporated by reference.

FIELD OF THE INVENTION

The present invention relates to a process for the preparation of an alkylene carbonate and/or an alkylene glycol from an alkene.

BACKGROUND OF THE INVENTION

Monoethylene glycol is used as a raw material in the manufacture of polyester fibres, polyethylene terephthalate (PET) plastics and resins. It is also incorporated into automobile antifreeze liquids. Ethylene carbonate is typically used as a solvent.

Monoethylene glycol is typically prepared from ethylene oxide, which is in turn prepared from ethylene. Ethylene and oxygen are passed over a silver catalyst, producing a product stream typically comprising ethylene oxide, unreacted ethylene, unreacted oxygen, reaction modifiers, carbon dioxide and water. The amount of ethylene oxide in the product stream is usually between about 0.5 and 10 mole percent. The product stream is supplied to an ethylene oxide absorber and the ethylene oxide is absorbed by a recirculating solvent stream containing mostly water. The ethylene oxide-depleted stream is partially or entirely supplied to a carbon dioxide absorption column wherein the carbon dioxide is at least partially absorbed by a recirculating absorbent stream. Gases that are not absorbed by the recirculating absorbent stream are recombined with any gases bypassing the carbon dioxide absorption column and are recycled to the ethylene oxide reactor.

The solvent stream leaving the ethylene oxide absorber is referred to as fat absorbent. Typically, the fat absorbent is supplied to an ethylene oxide stripper, wherein ethylene oxide is removed from the fat absorbent as a vapour stream. The ethylene oxide-depleted solvent stream exiting the ethylene oxide stripper is referred to as lean absorbent and is recirculated to the ethylene oxide absorber to absorb further ethylene oxide.

The ethylene oxide obtained from the ethylene oxide stripper can be purified for storage and sale or can be further reacted to provide ethylene glycol. In one well-known process, ethylene oxide is reacted with a large excess of water in a non-catalytic process. This reaction typically produces a glycol product stream consisting of almost 90 weight percent monoethylene glycol, the remainder being predominantly diethylene glycol, some triethylene glycol and a small amount of higher homologues. In another well-known process, ethylene oxide is catalytically reacted with carbon dioxide to produce ethylene carbonate. The ethylene carbonate may be subsequently hydrolysed to provide ethylene glycol. Reaction via ethylene carbonate significantly improves the selectivity of ethylene oxide conversion to monoethylene glycol.

Efforts have been made to simplify the process for obtaining ethylene glycol from ethylene, reducing the equipment that is required and reducing the energy consumption. GB 2 107 712 describes a process for preparing monoethylene glycol wherein the gases from the ethylene oxide reactor are supplied directly to a reactor wherein ethylene oxide is converted to ethylene carbonate or to a mixture of ethylene glycol and ethylene carbonate. EP 776 890 describes a process wherein the gases from the ethylene oxide reactor are supplied to an absorber wherein the absorbing solution mainly contains ethylene carbonate and ethylene glycol. The ethylene oxide in the absorbing solution is supplied to a carboxylation reactor and allowed to react with carbon dioxide in the presence of a carboxylation catalyst. The ethylene carbonate in the absorbing solution is subsequently supplied with the addition of water to a hydrolysis reactor and subjected to hydrolysis in the presence of a hydrolysis catalyst.

The present inventors have sought to further improve the manufacture of an alkylene carbonate and/or an alkylene glycol from an alkene.

SUMMARY OF THE INVENTION

Accordingly, the present invention provides a reaction system for the production of an alkylene carbonate and/or an alkylene glycol comprising:
  an epoxidation zone containing an epoxidation catalyst located within an epoxidation reactor;
  a carboxylation zone containing an iodide-containing carboxylation catalyst located within an alkylene oxide absorber; and
  one or more purification zones containing a purification absorbent capable of reducing the quantity of iodide-containing impurities in a feed comprising a recycle gas, which purification zones are located upstream from the epoxidation zone.

The present invention also provides a process for the production of an alkylene
carbonate and/or an alkylene glycol comprising:
  contacting an epoxidation feed comprising an alkene, oxygen, and an epoxidation recycle gas with an epoxidation catalyst in an epoxidation reactor to yield an epoxidation reaction product comprising an alkylene oxide;
  contacting the epoxidation reaction product with a lean absorbent in the presence of an iodide-containing carboxylation catalyst in an alkylene oxide absorber to yield the epoxidation recycle gas and a fat absorbent containing alkylene carbonate and/or alkylene glycol; and
  contacting at least a portion of the epoxidation recycle gas with a purification absorbent capable of reducing the quantity of iodide-containing impurities prior to contacting with the epoxidation catalyst.

In the process of the invention, the alkylene oxide absorber acts both as an absorber, absorbing alkylene oxide from the epoxidation reaction product, and as a reactor, converting alkylene oxide to alkylene carbonate and/or alkylene glycol. Such absorbers are conventionally used for mass transfer processes rather than chemical reactions. In the process of the present invention, carboxylation occurs in the alkylene oxide absorber. Typical carboxylation catalysts are iodide-containing catalysts. It has been found that performing the carboxylation reaction in the alkylene oxide absorber using an iodide-containing carboxylation catalyst can result in iodide-containing impurities being introduced into the recycle gas stream. Such iodide-containing impurities can act as poisons to the epoxidation catalyst. It has been found that contacting the recycle gas stream with a purification absorbent capable of reducing the quantity of iodide-containing impurities improves the epoxidation process, in particular improves the selectivity, activity, and duration of time the epoxidation catalyst remains in the reactor tubes before having to exchange the catalyst with a fresh epoxidation catalyst.

DETAILED DESCRIPTION OF THE INVENTION

Figure 1:
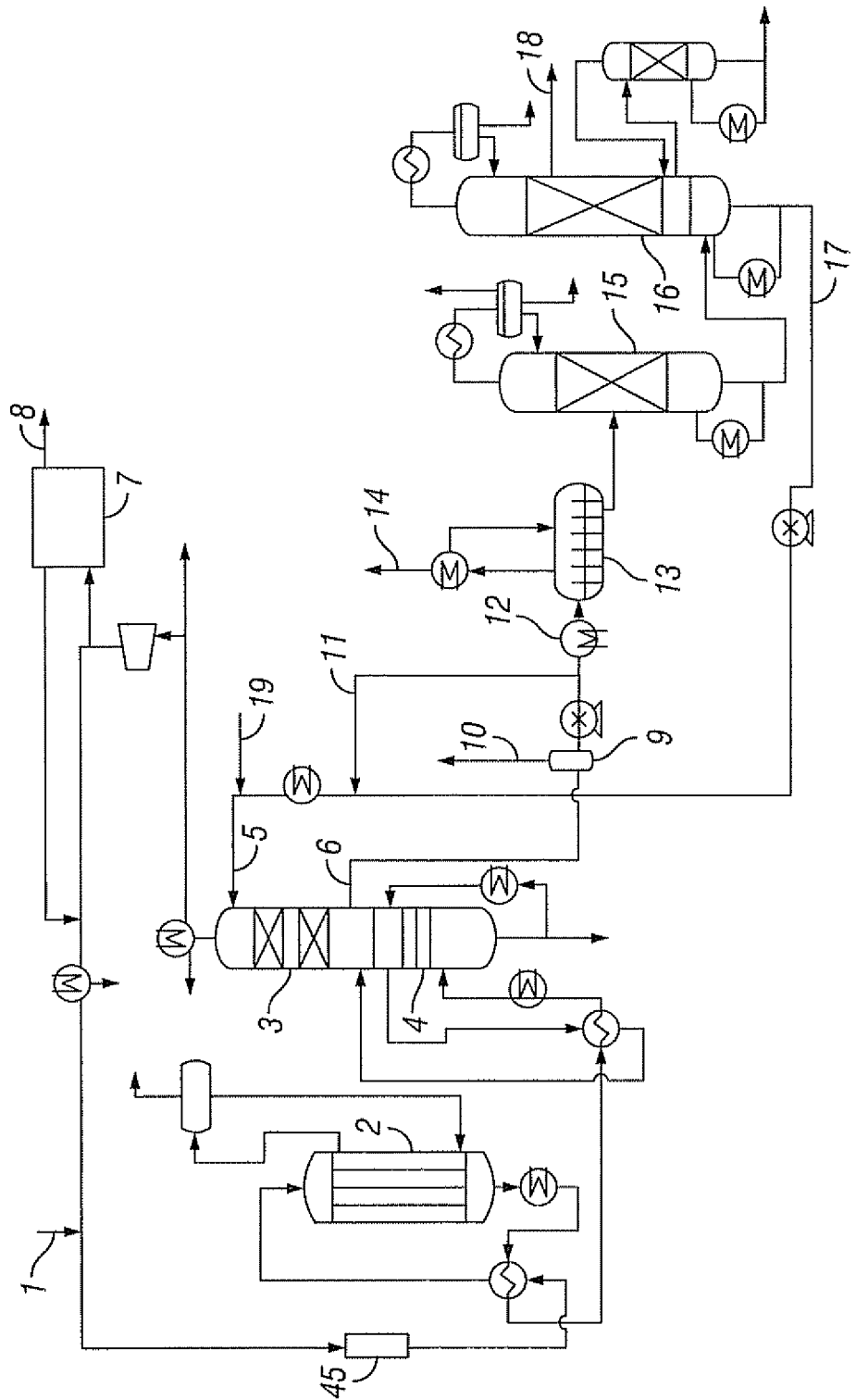
FIG. 1 is a schematic diagram showing a process according to an embodiment of the invention.

The present invention provides a process for the preparation of an alkylene carbonate and/or an alkylene glycol from an alkene:

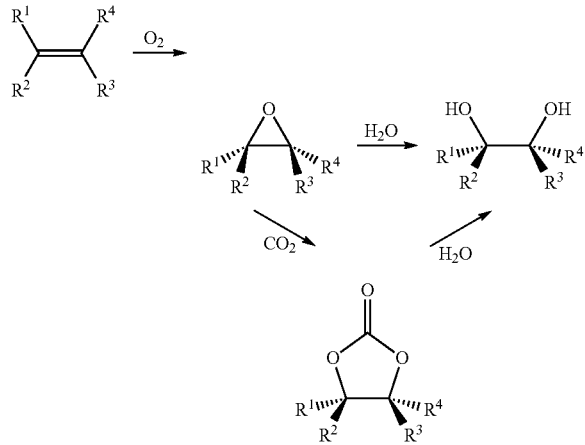

$R^1$, $R^2$, $R^3$ and $R^4$ are preferably chosen from hydrogen or an optionally substituted alkyl group having from 1 to 6 carbon atoms, more preferably from 1 to 3 carbon atoms. As substituents, moieties such as hydroxy groups may be present. Preferably, $R^1$, $R^2$ and $R^3$ represent hydrogen atoms and $R^4$ represents hydrogen or a non-substituted $C_1$-$C_3$-alkyl group and, more preferably, $R^1$, $R^2$, $R^3$ and $R^4$ all represent hydrogen atoms.

Examples of suitable alkenes therefore include ethylene and propylene. In the present invention the most preferred alkene is ethylene.

The epoxidation reactor vessel of the present invention may be any reactor vessel used to react a feed containing alkene and oxygen. The epoxidation reactor vessel may contain one or more open-ended reactor tubes. Preferably, the epoxidation reactor vessel is a shell-and-tube heat exchanger containing a plurality of reactor tubes. The reactor tubes may preferably have an internal diameter in the range of from 15 to 80 mm (millimeters), more preferably from 20 to 75 mm, and most preferably from 25 to 70 mm. The reactor tubes may preferably have a length in the range of from 5 to 20 m (meters), more preferably from 10 to 15 m. The shell-and-tube heat exchanger may contain from 1000 to 20000 reactor tubes, in particular from 2500 to 15000 reactor tubes.

The one or more reactor tubes are positioned substantially parallel to the central longitudinal axis of the reactor vessel and are surrounded by a shell adapted to receive a heat exchange fluid (i.e., the shell side of the shell-and-tube heat exchanger). The heat exchange fluid in the heat exchange chamber may be any fluid suitable for heat transfer, for example water or an organic material suitable for heat exchange. The organic material may be an oil or kerosene. The upper ends of the one or more reactor tubes are connected to a substantially horizontal upper tube plate and are in fluid communication with the one or more inlets to the reactor vessel, and the lower ends of the one or more reactor tubes are connected to a substantially horizontal lower tube plate and are in fluid communication with the one or more outlets to the epoxidation reactor vessel (i.e., the tube side of the shell-and-tube heat exchanger). The epoxidation reactor vessel contains an epoxidation zone comprising a packed bed of catalyst particles. The catalyst bed is positioned inside the one or more reactor tubes.

The purification of the feed components, in particular the recycle gas, occurs within one or more purification zones located outside of the epoxidation reactor vessel and/or within a purification zone positioned inside of the epoxidation reactor vessel.

The terms "substantially vertical" and "substantially horizontal", as used herein, are understood to include minor deviations from true vertical or horizontal positions relative to the central longitudinal axis of the reactor vessel, in particular the terms are meant to include variations ranging from 0 to 20 degrees from true vertical or horizontal positions. True vertical is aligned along the central longitudinal axis of the reactor vessel. True horizontal is aligned perpendicular to the central longitudinal axis of the reactor vessel.

The term "substantially parallel", as used herein, is understood to include minor deviations from a true parallel position relative to the central longitudinal axis of the reactor vessel, in particular the term is meant to include variations ranging from 0 to 20 degrees from a true parallel position relative to the central longitudinal axis of the reactor vessel.

As used herein, the purification absorbent temperature is deemed to be the weight average temperature of the purification absorbent particles in the packed bed.

As used herein, the epoxidation catalyst temperature is deemed to be the weight average temperature of the epoxidation catalyst particles in the packed bed.

In an embodiment, one or more purification zones are located outside of the epoxidation reactor vessel (i.e., separate from the epoxidation reactor vessel). The recycle gas is fed to one or more purification zones before contacting the epoxidation catalyst. One or more additional feed components may also be contacted with the purification absorbent in a purification zone either in conjunction with or separate from the recycle gas. A purification zone may comprise one or more separate purification vessels each containing a packed bed of the purification absorbent.

In this embodiment, the one or more purification zones are located upstream from the epoxidation reactor vessel. Preferably, at least one purification zone is located in the recycle gas loop. The recycle gas loop comprises interconnecting pipework between the alkylene oxide absorber and the epoxidation reactor vessel and optionally includes a carbon dioxide absorber, heat exchangers, compressors, and water removal "knock-out" vessels in the recycle gas loop. Suitably, one or more purification zones may be located anywhere in the recycle gas loop, for example in the recycle gas loop downstream from the addition of the feed components (e.g., ethylene, oxygen, methane and reaction modifier) and upstream from the product/feed heat exchanger which exchanges the heat from the epoxidation reaction product with the feed components to the epoxidation reactor; in the recycle gas loop between the product/feed heat exchanger and the inlet to the epoxidation reactor; in the recycle gas loop upstream from any "knock-out" vessels used to remove water from the recycle gas; in the recycle gas loop between the alkylene oxide absorber and the carbon dioxide absorber, in particular in the recycle gas loop between the alkylene oxide absorber and a compressor positioned in the recycle gas loop prior to the carbon dioxide absorber.

In this embodiment, the packed bed of the purification absorbent in the purification vessel may have any bed height. A purification zone may comprise two or more separate purification vessels. The two or more purification vessels may be arranged in parallel with associated switching means to allow the process to be switched between purification vessels, thus maintaining a continuous operation of the process. Suitable switching means that can be used in this embodiment are known to the skilled person.

In this embodiment, suitably the temperature of the purification absorbent may be at least 25° C., in particular at least 60° C., more in particular at least 70° C. The temperature of the purification absorbent may be at most 325° C., in particular at most 210° C., more in particular at most 200° C., most in particular at most 180° C. In this embodiment, the temperature of the purification absorbent may be in the range of from 25 to 325° C., preferably from 60 to 200° C., most preferably from 70 to 180° C.

In an embodiment, the epoxidation reactor vessel may contain a purification zone comprising a packed bed of purification absorbent positioned upstream from the one or more reactor tubes, for example positioned on top of the upper tube plate and reactor tubes in the headspace of the epoxidation reactor vessel. In this embodiment, the total epoxidation reactor feed, which includes the recycle gas, is contacted with the purification absorbent. In this embodiment, the packed bed of purification absorbent may have a bed height of at least 0.05 m, in particular at least 0.075 m, more in particular at least 0.1 m, most in particular at least 0.15 m. In this embodiment, the purification absorbent may have a bed height of at most 2 m, in particular at most 1 m, more in particular at most 0.5 m. In this embodiment, suitably the temperature of the purification absorbent may be at least 130° C., more in particular at least 140° C. The temperature of the purification absorbent may be at most 210° C., in particular at most 200° C., more in particular at most 180° C. The temperature of the purification absorbent may be in the range of from 130 to 210° C., preferably from 140 to 200° C., most preferably from 145 to 180° C.

In an embodiment, the epoxidation reactor vessel may contain a purification zone comprising a packed bed of purification absorbent positioned within the reactor tubes upstream from the epoxidation zone containing the epoxidation catalyst. In this embodiment, the total epoxidation reactor feed, which includes the recycle gas, is contacted with the purification absorbent. In this embodiment, the packed bed of purification absorbent may have a bed height of at least 0.25% of the length of the reactor tube, in particular at least 0.5%, more in particular at least 1%, most in particular at least 2% of the length of the reactor tube. In this embodiment, the purification absorbent may have a bed height of at most 20% of the length of the reactor tube, in particular at most 15%, more in particular at most 10%, most in particular at most 5% of the length of the reactor tube. In this embodiment, suitably the temperature of the purification absorbent when positioned within the reactor tubes may be at least 140° C., in particular at least 150° C., more in particular at least 180° C. The temperature of the purification absorbent may be at most 300° C., in particular at most 290° C., more in particular at most 280° C. In this embodiment, the temperature of the purification absorbent may be in the range of from 150 to 300° C., preferably from 180 to 285° C., most preferably from 210 to 270° C.

The iodide-containing impurities may be removed from the recycle gas and optionally one or more additional feed components before or after the addition of an organic chloride reaction modifier to the epoxidation feed, preferably before the addition of the organic chloride reaction modifier.

The purification absorbent is any absorbent capable of reducing the quantity of iodide-containing impurities in a fluid stream, in particular an epoxidation recycle gas stream. Without wishing to be bound by theory, it is believed the absorbent reduces the impurities in the feed by chemical or physical means including, but not limited to, reaction with the impurities and absorption of the impurities. The size and shape of the purification absorbent is not critical to the invention and may be in the form of chunks, pieces, cylinders, rings, spheres, wagon wheels, tablets, trilobes, and the like of a size suitable for employment in a fixed bed, for example from 2 mm to 30 mm.

As used herein, unless otherwise specified, the weight of the purification absorbent is deemed to be the total weight of the purification absorbent including the weight of any support material present in the purification absorbent.

In an embodiment, the purification absorbent may be a spent epoxidation catalyst. The term "spent epoxidation catalyst", as used herein, is understood to refer to an epoxidation catalyst which has produced more olefin oxide than the epoxidation catalyst contained in the epoxidation zone. In some embodiments, the spent epoxidation catalyst has produced at least 1 $kT/m^3$, preferably at least 1.6 $kT/m^3$, in particular at least 2 $kT/m^3$.

In this embodiment, the purification absorbent may be prepared by conventional processes for the production of such metal-containing materials, for example by precipitation or impregnation. The resulting salts may then be contacted with a basic bicarbonate or carbonate solution in a pH range of from 6 to 9 at a temperature from 15 to 90° C., in particular 80° C., to produce a precipitate of metal oxide. The precipitate may be filtered and then washed at a temperature in the range of from 20 to 50° C. The precipitate may then be dried at a temperature in the range of from 100 to 160° C., in particular 120 to 150° C. After drying, the precipitate may then be calcined at a temperature in the range of from 170 to 600° C., in particular from 350 to 550°

C. The precipitate may be formed into a desired size and shape by conventional processes such as extrusion or tableting. Alternatively, an impregnation process may be used to form the purification absorbent by impregnating the support material with suitable solutions of the metal compounds followed by drying and calcining.

In this embodiment, the purification absorbent after calcination may contain metal oxide in a quantity in the range of from 20 to 100% w (percent by weight), relative to the weight of the purification absorbent, in particular from 70 to 100% w, relative to the weight of the purification absorbent, more in particular from 75 to 95% w, relative to the weight of the purification absorbent.

In this embodiment, the support material may be present in the purification absorbent after calcination in a quantity of at least 1% w, relative to the weight of the purification absorbent, in particular at least 1.5% w, more in particular at least 2% w, relative to the weight of the purification absorbent. The support material may be present in the purification absorbent after calcination in a quantity of at most 80% w, relative to the weight of the purification absorbent, in particular at most 50% w, more in particular at most 30% w, relative to the weight of the purification absorbent, most in particular at most 25% w, relative to the weight of the purification absorbent. The support material may be present in the purification absorbent after calcination in a quantity in the range of from 5 to 25% w, in particular from 10 to 20% w, relative to the weight of the purification absorbent.

In an embodiment, the purification absorbent may comprise silver, an alkali or alkaline earth metal component, and a support material. When using purification absorbents which contain silver, higher temperatures are preferably avoided when ethylene and oxygen are present in the feed to be treated.

In this embodiment, the purification absorbent may be prepared by co-mulling the components of the purification absorbent. For further description of such co-mulling methods, reference may be made to US 2006/0036104, which is hereby incorporated by reference. Preferably, the silver and the alkali or alkaline earth metal components are deposited on the support material through an impregnation method. For further description of such impregnation methods, reference may be made to U.S. Pat. No. 5,380,697, U.S. Pat. No. 5,739,075, EP-A-266015, and U.S. Pat. No. 6,368,998, which methods are incorporated herein by reference. Methods of depositing silver on a support material include impregnating the support with a silver compound containing cationic silver or complexed silver and optionally performing a reduction to form metallic silver particles. Suitably, silver dispersions, for example silver sols, may be used to deposit silver on the support material.

In this embodiment, the purification absorbent may contain silver in a quantity of at least 5 g/kg, in preferably at least 100 g/kg, more preferably at least 150 g/kg, most preferably at least 200 g/kg, relative to the weight of the purification absorbent. Preferably, the purification absorbent comprises silver in a quantity of from 5 to 500 g/kg, more preferably from 150 to 400 g/kg, for example 105 g/kg, or 120 g/kg, or 190 g/kg, or 250 g/kg, or 350 g/kg, on the same basis.

In this embodiment, the support material may be selected from alumina, titania, zirconia, silica, activated carbon or mixtures thereof. Preferably, the support material may be alumina, in particular gamma-alumina. In this embodiment, the support material has a surface area of more than 20 $m^2/g$, preferably at least 25 $m^2/g$, more preferably at least 50 $m^2/g$, most preferably at least 75 $m^2/g$, in particular at least 100 $m^2/g$, more in particular at least 125 $m^2/g$. The support material may have a surface area of at most 1200 $m^2/g$, preferably at most 300 $m^2/g$, more preferably at most 200 $m^2/g$, most preferably at most 175 $m^2/g$.

In this embodiment, the purification absorbent may have a quantity of silver relative to the surface area of the support material (i.e., silver density) of less than 0.025 g $Ag/m^2$, preferably at most 0.01 g $Ag/m^2$, more preferably at most 0.005 g $Ag/m^2$. The purification absorbent may have a silver density of at least $1\times10^{-5}$ g $Ag/m^2$, preferably at least $5\times10^{-5}$ g $Ag/m^2$, more preferably at least $1\times10^{-4}$ g $Ag/m^2$. In this embodiment, it is preferred that the purification absorbent has a lower silver density than the silver density of the epoxidation catalyst.

In this embodiment, the purification absorbent comprises an alkali or alkaline earth metal component. Preferably, the alkali metal may be selected from sodium, potassium, lithium, rubidium, cesium, and combinations thereof, in particular sodium and potassium. Preferably, the alkaline earth metal may be selected from calcium, magnesium, strontium, barium, and combinations thereof. The alkali metal component may suitably be provided in salt or base form. Suitable alkali metal salts may include, but are not limited to, nitrates, oxalates, citrates, acetates, carbonates, and the like. Preferably, the alkali metal component may be in the form of a nitrate, hydroxide, carbonate, chloride, or bicarbonate. The alkaline earth metal component may suitably be provided in salt or base form. Suitable alkaline earth metal salts may include, but are not limited to, nitrates, oxalates, citrates, acetates, carbonates, chlorides, and the like. Preferably, the alkaline earth metal component may be in the form of a hydroxide. Without wishing to be bound by theory, it is believed that the alkali or alkaline earth metals present in the purification absorbent reduce the amount of acidic sites present on the surface of the support material which can react with a hydrocarbon such as an alkene, forming unwanted by-products in the feed.

In this embodiment, the alkali or alkaline earth metals may be present in a total quantity of at least 0.1 mmole/kg, more typically at least 1 mmole/kg, in particular at least 10 mmole/kg, more in particular at least 50 mmole/kg, most in particular at least 100 mmole/kg, calculated as the total quantity of the elements (for example sodium, potassium, rubidium, cesium, magnesium, calcium, strontium, and barium) relative to the weight of the purification absorbent. The alkali or alkaline earth metals may be present in a quantity of at most 5000 mmole/kg, preferably at most 500 mmole/kg, more preferably at most 300 mmole/kg, calculated as the total quantity of the elements relative to the weight of the purification absorbent.

In a separate embodiment, the purification absorbent may comprise a basic zeolite. Basic zeolites may include any basic zeolites capable of reducing iodide-containing impurities from a feed. Zeolites belong to a class of highly structured alumina silicates. Most zeolites are made artificially, but some are found as minerals in nature. The porous structure of zeolites consists of a crystal lattice in which oxygen, silicon, and aluminum atoms are placed. Commercial zeolites are categorized, depending on the structure and functionality, as P-, A-, X-, and Y-zeolites. Basic zeolites are characterized by low silicon/aluminum molar ratios and by the presence of weakly electronegative alkaline cations. Suitably, the basic zeolites have a Si:Al ratio of from 1:1 to 6:1, in particular from 1:1 to 2.5:1. Well known methods of ion exchange and impregnation may be used to prepare basic zeolites. Useful ion-exchange compounds may include alkali metal cation containing materials and alkaline earth metal cation containing materials.

In a separate embodiment, the purification absorbent may comprise an alkali metal or alkaline earth metal carbonate. Suitably, the alkali metal may include sodium, potassium, rubidium, and cesium, in particular sodium, potassium and cesium. Suitably, the alkaline earth metal may include magnesium, calcium, strontium, and barium, in particular magnesium and calcium.

In a separate embodiment, the purification absorbent may comprise silver oxide. In this embodiment, the purification absorbent may additionally comprise a support material. In this embodiment, the support material may include natural or artificial inorganic materials, such as refractory materials, silicon carbide, clays, zeolites, charcoal, and alkaline earth metal carbonates, such as magnesium carbonate and calcium carbonate. Suitably, the refractory materials may include alumina, magnesia, zirconia, silica, and mixtures thereof. When a support material is used, the purification absorbent may be prepared using various techniques including co-mulling, impregnating, and co-precipitating methods. Such methods are well known to the skilled person.

The epoxidation reactor vessel contains an epoxidation zone comprising an epoxidation catalyst bed. In the normal practice of this invention, a major portion of the epoxidation catalyst bed comprises epoxidation catalyst particles. By a "major portion" it is meant that the ratio of the weight of the epoxidation catalyst particles to the weight of all the particles contained in the epoxidation catalyst bed is at least 0.50, in particular at least 0.8, preferably at least 0.85, more preferably at least 0.9. Particles which may be contained in the epoxidation catalyst bed other than the epoxidation catalyst particles are, for example, inert particles; however, it is preferred that such other particles are not present in the epoxidation catalyst bed. The epoxidation catalyst bed is supported in the one or more reactor tubes by a catalyst support means arranged in the lower ends of the reactor tubes. The support means may include a screen or a spring.

The epoxidation catalyst bed may have any bed height. Suitably, the epoxidation catalyst bed may have a bed height of 100% of the length of the reactor tube, when a purification zone is not located within the reactor tubes. The epoxidation catalyst bed may suitably have a bed height of at most 95% or at most 90%, or at most 85%, or at most 80% of the length of the reactor tube. The epoxidation catalyst bed may suitably have a bed height of least 10% of the length of the reactor tube, in particular at least 25%, more in particular at least 50% of the length of the reactor tube.

The one or more reactor tubes may also contain a separate bed of particles of an inert material for the purpose of, for example, heat exchange with a feedstream. The one or more reactor tubes may also contain another such separate bed of inert material for the purpose of, for example, heat exchange with the epoxidation reaction product. Alternatively, rod-shaped metal inserts may be used in place of the bed of inert material. For further description of such inserts, reference is made to U.S. Pat. No. 7,132,555, which description is incorporated by reference.

Suitably, the temperature of the epoxidation catalyst in the epoxidation zone may be at least 150° C., in particular at least 180° C., more in particular at least 220° C. The temperature of the epoxidation catalyst bed in the epoxidation zone may be at most 325° C., in particular at most 300° C. The temperature of the epoxidation catalyst bed in the epoxidation zone may be in the range of from 180 to 325° C., preferably from 200 to 300° C.

The catalyst typically used for the epoxidation of an alkene is a catalyst comprising silver deposited on a carrier. The size and shape of the epoxidation catalyst is not critical to the invention and may be in the form of chunks, pieces, cylinders, rings, spheres, wagon wheels, tablets, and the like of a size suitable for employment in a fixed bed shell-and-tube heat exchanger reactor vessel, for example from 2 mm to 20 mm.

The carrier may be based on a wide range of materials. Such materials may be natural or artificial inorganic materials and they may include refractory materials, silicon carbide, clays, zeolites, charcoal, and alkaline earth metal carbonates, for example calcium carbonate. Preferred are refractory materials, such as alumina, magnesia, zirconia, silica, and mixtures thereof. The most preferred material is α-alumina. Typically, the carrier comprises at least 85% w, more typically at least 90% w, in particular at least 95% w α-alumina, frequently up to 99.9% w α-alumina, relative to the weight of the carrier. Other components of the α-alumina carrier may comprise, for example, silica, titania, zirconia, alkali metal components, for example sodium and/or potassium components, and/or alkaline earth metal components, for example calcium and/or magnesium components.

The surface area of the carrier may suitably be at least 0.1 m$^2$/g, preferably at least 0.3 m$^2$/g, more preferably at least 0.5 m$^2$/g, and in particular at least 0.6 m$^2$/g, relative to the weight of the carrier; and the surface area may suitably be at most 10 m$^2$/g, preferably at most 6 m$^2$/g, and in particular at most 4 m$^2$/g, relative to the weight of the carrier. "Surface area" as used herein is understood to relate to the surface area as determined by the B.E.T. (Brunauer, Emmett and Teller) method as described in Journal of the American Chemical Society 60 (1938) pp. 309-316. High surface area carriers, in particular when they are alpha alumina carriers optionally comprising in addition silica, alkali metal and/or alkaline earth metal components, provide improved performance and stability of operation.

The water absorption of the carrier may suitably be at least 0.2 g/g, preferably at least 0.25 g/g, more preferably at least 0.3 g/g, most preferably at least 0.35 g/g; and the water absorption may suitably be at most 0.85 g/g, preferably at most 0.7 g/g, more preferably at most 0.65 g/g, most preferably at most 0.6 g/g. The water absorption of the carrier may be in the range of from 0.2 to 0.85 g/g, preferably in the range of from 0.25 to 0.7 g/g, more preferably from 0.3 to 0.65 g/g, most preferably from 0.3 to 0.6 g/g. A higher water absorption may be in favor in view of a more efficient deposition of the metal and promoters, if any, on the carrier by impregnation. However, at a higher water absorption, the carrier, or the catalyst made therefrom, may have lower crush strength. As used herein, water absorption is deemed to have been measured in accordance with ASTM C20, and water absorption is expressed as the weight of the water that can be absorbed into the pores of the carrier, relative to the weight of the carrier.

The preparation of the epoxidation catalyst comprising silver is known in the art and the known methods are applicable to the preparation of the shaped catalyst particles which may be used in the practice of this invention. Methods of depositing silver on the carrier include impregnating the carrier with a silver compound containing cationic silver and/or complexed silver and performing a reduction to form metallic silver particles. For further description of such methods, reference may be made to U.S. Pat. No. 5,380,697, U.S. Pat. No. 5,739,075, EP-A-266015, and U.S. Pat. No. 6,368,998, which methods are incorporated herein by reference. Suitably, silver dispersions, for example silver sols, may be used to deposit silver on the carrier.

The reduction of cationic silver to metallic silver may be accomplished during a step in which the epoxidation catalyst is dried, so that the reduction as such does not require a separate process step. This may be the case if the silver containing impregnation solution comprises a reducing agent, for example, an oxalate, a lactate or formaldehyde.

Appreciable catalytic activity may be obtained by employing a silver content of the epoxidation catalyst of at least 10 g/kg, relative to the weight of the catalyst. Preferably, the epoxidation catalyst comprises silver in a quantity of from 50 to 500 g/kg, more preferably from 100 to 400 g/kg, for example 105 g/kg, or 120 g/kg, or 190 g/kg, or 250 g/kg, or 350 g/kg, on the same basis. As used herein, unless otherwise specified, the weight of the epoxidation catalyst is deemed to be the total weight of the catalyst including the weight of the carrier and catalytic components.

The epoxidation catalyst for use in this invention may comprise a promoter component which comprises an element selected from rhenium, tungsten, molybdenum, chromium, nitrate- or nitrite-forming compounds, and combinations thereof. Preferably the promoter component comprises, as an element, rhenium. The form in which the promoter component may be deposited onto the carrier is not material to the invention. Rhenium, molybdenum, tungsten, chromium or the nitrate- or nitrite-forming compound may suitably be provided as an oxyanion, for example, as a perrhenate, molybdate, tungstate, or nitrate, in salt or acid form.

The promoter component may typically be present in a quantity of at least 0.1 mmole/kg, more typically at least 0.5 mmole/kg, in particular at least 1 mmole/kg, more in particular at least 1.5 mmole/kg, calculated as the total quantity of the element (that is rhenium, tungsten, molybdenum and/or chromium) relative to the weight of the catalyst. The promoter component may be present in a quantity of at most 50 mmole/kg, preferably at most 10 mmole/kg, calculated as the total quantity of the element relative to the weight of the catalyst.

When the epoxidation catalyst comprises rhenium as the promoter component, the epoxidation catalyst may preferably comprise a rhenium co-promoter, as a further component deposited on the carrier. Suitably, the rhenium co-promoter may be selected from components comprising an element selected from tungsten, chromium, molybdenum, sulfur, phosphorus, boron, and combinations thereof. Preferably, the rhenium co-promoter is selected from tungsten, chromium, molybdenum, sulfur, and combinations thereof. It is particularly preferred that the rhenium co-promoter comprises, as an element, tungsten and/or sulfur.

The rhenium co-promoter may typically be present in a total quantity of at least 0.1 mmole/kg, more typically at least 0.25 mmole/kg, and preferably at least 0.5 mmole/kg, calculated as the element (i.e. the total of tungsten, chromium, molybdenum, sulfur, phosphorus and/or boron), relative to the weight of the catalyst. The rhenium co-promoter may be present in a total quantity of at most 40 mmole/kg, preferably at most 10 mmole/kg, more preferably at most 5 mmole/kg, on the same basis. The form in which the rhenium co-promoter may be deposited on the carrier is not material to the invention. For example, it may suitably be provided as an oxide or as an oxyanion, for example, as a sulfate, borate or molybdate, in salt or acid form.

The epoxidation catalyst preferably comprises silver, the promoter component, and a component comprising a further element, deposited on the carrier. Eligible further elements may be selected from the group of nitrogen, fluorine, alkali metals, alkaline earth metals, titanium, hafnium, zirconium, vanadium, thallium, thorium, tantalum, niobium, gallium and germanium and combinations thereof. Preferably the alkali metals are selected from lithium, potassium, rubidium and cesium. Most preferably the alkali metal is lithium, potassium and/or cesium. Preferably the alkaline earth metals are selected from calcium, magnesium and barium. Typically, the further element is present in the epoxidation catalyst in a total quantity of from 0.01 to 500 mmole/kg, more typically from 0.05 to 100 mmole/kg, calculated as the element, relative to the weight of the catalyst. The further elements may be provided in any form. For example, salts of an alkali metal or an alkaline earth metal are suitable. For example, lithium compounds may be lithium hydroxide or lithium nitrate.

Preferred amounts of the components of the epoxidation catalysts are, when calculated as the element, relative to the weight of the catalyst:

silver from 10 to 500 g/kg,
rhenium from 0.01 to 50 mmole/kg, if present,
the further element or elements, if present, each from 0.1 to 500 mmole/kg, and,
the rhenium co-promoter from 0.1 to 30 mmole/kg, if present.

As used herein, the quantity of alkali metal present in the catalyst or absorbent is deemed to be the quantity insofar as it can be extracted from the catalyst or absorbent with de-ionized water at 100° C. The extraction method involves extracting a 10-gram sample of the catalyst or absorbent three times by heating it in 20 ml portions of de-ionized water for 5 minutes at 100° C. and determining in the combined extracts the relevant metals by using a known method, for example atomic absorption spectroscopy.

As used herein, the quantity of alkaline earth metal present in the catalyst or absorbent is deemed to be the quantity insofar as it can be extracted from the catalyst or absorbent with 10% w nitric acid in de-ionized water at 100° C. The extraction method involves extracting a 10-gram sample of the catalyst or absorbent by boiling it with a 100 ml portion of 10% w nitric acid for 30 minutes (1 atm., i.e. 101.3 kPa) and determining in the combined extracts the relevant metals by using a known method, for example atomic absorption spectroscopy. Reference is made to U.S. Pat. No. 5,801,259, which is incorporated herein by reference.

Although the present epoxidation process may be carried out in many ways, it is preferred to carry it out as a gas phase process, i.e. a process in which an epoxidation reaction feed is contacted in the gas phase with the epoxidation catalyst to yield an epoxidation reaction product comprising an alkylene oxide. The term "epoxidation reaction product", as used herein, is understood to refer to the fluid exiting from the outlet of the epoxidation reactor vessel. Generally the process is carried out as a continuous process.

The epoxidation feed components include an alkene, oxygen, and an epoxidation recycle gas. Additional epoxidation feed components may include an organic chloride reaction modifier, a nitrogen-containing reaction modifier, a saturated hydrocarbon, and an inert dilution gas.

The quantity of alkene present in the epoxidation feed may be selected within a wide range. Typically, the quantity of alkene present in the epoxidation feed may be at most 80 mole-%, relative to the total epoxidation feed. Preferably, it may be in the range of from 0.5 to 70 mole-%, in particular from 1 to 60 mole-%, more in particular from 15 to 40 mole-%, on the same basis.

The present epoxidation process may be air-based or oxygen-based, see "Kirk-Othmer Encyclopedia of Chemical Technology", $3^{rd}$ edition, Volume 9, 1980, pp. 445-447. In the air-based process, air or air enriched with oxygen is employed as the source of the oxidizing agent while in the oxygen-based processes high-purity (at least 95 mole-%) oxygen or very high purity (at least 99.5 mole-%) oxygen is employed as the source of the oxidizing agent. Reference may be made to U.S. Pat. No. 6,040,467, incorporated by reference, for further description of oxygen-based processes. Presently most epoxidation plants are oxygen-based and this is a preferred embodiment of the present invention.

The quantity of oxygen present in the epoxidation feed may be selected within a wide range. However, in practice, oxygen is generally applied in a quantity which avoids the flammable regime. Oxygen may be present in a quantity of at least 0.5 mole-%, relative to the total epoxidation feed, in particular at least 1 mole-%, more in particular at least 2 mole-%, most in particular at least 5 mole-%, relative to the total epoxidation feed. Oxygen may be present in a quantity of at most 25 mole-%, relative to the total epoxidation feed, in particular at most 20 mole-%, more in particular at most 15 mole-%, most in particular at most 12 mole-%, relative to the total epoxidation feed In order to remain outside the flammable regime, the quantity of oxygen in the epoxidation feed may be lowered as the quantity of the alkene is increased. The actual safe operating ranges depend, along with the epoxidation feed composition, also on the reaction conditions such as the reaction temperature and the pressure.

An organic chloride reaction modifier may be present in the epoxidation feed for increasing the selectively, suppressing the undesirable oxidation of alkene or alkylene oxide to carbon dioxide and water, relative to the desired formation of alkylene oxide.

Preferred organic chloride reaction modifiers are chlorohydrocarbons. More preferably they are selected from the group of methyl chloride, ethyl chloride, ethylene dichloride, vinyl chloride or a mixture thereof. Most preferred organic chloride reaction modifiers are ethyl chloride and ethylene dichloride.

The epoxidation feed may include a nitrogen-containing reaction modifier. Nitrogen oxides, organic nitro compounds such as nitromethane, nitroethane, and nitropropane, hydrazine, hydroxylamine or ammonia may be employed. It is frequently considered that under the operating conditions of alkene epoxidation the nitrogen containing reaction modifiers are precursors of nitrates or nitrites, i.e. they are so-called nitrate- or nitrite-forming compounds (cf. e.g. EP-A-3642 and U.S. Pat. No. 4,822,900, which are incorporated herein by reference).

Suitable nitrogen oxides are of the general formula $NO_x$ wherein x is in the range of from 1 to 2.5, and include for example NO, $N_2O_3$, $N_2O_4$, and $N_2O_5$. Suitable organic nitrogen compounds are nitro compounds, nitroso compounds, amines, nitrates and nitrites, for example nitromethane, 1-nitropropane or 2-nitropropane.

The reaction modifiers are generally effective when used in small quantities in the epoxidation feed. The nitrogen-containing reaction modifier may be present in a quantity of at most $500 \times 10^{-4}$ mole-%, relative to the total epoxidation feed, in particular at most $400 \times 10^{-4}$ mole-%, more in particular at most $300 \times 10^{-4}$ mole-%, relative to the total epoxidation feed. The nitrogen-containing reaction modifier may be present in a quantity of at least $5 \times 10^{-4}$ mole-%, relative to the total epoxidation feed, in particular at least $10 \times 10^{-4}$ mole-%, more in particular at least $50 \times 10^{-4}$ mole-%, relative to the total epoxidation feed. When a nitrogen-containing reaction modifier is utilized in the epoxidation feed, the organic chloride may be present in a quantity of at most $500 \times 10^{-4}$ mole-%, relative to the total epoxidation feed, in particular at most $400 \times 10^{-4}$ mole-%, more in particular at most $300 \times 10^{-4}$ mole-%, relative to the total epoxidation feed. When a nitrogen-containing reaction modifier is utilized in the epoxidation feed, the organic chloride reaction modifier may be present in a quantity of at least $5 \times 10^{-4}$ mole-%, relative to the total epoxidation feed, in particular at least $10 \times 10^{-4}$ mole-%, more in particular at least $50 \times 10^{-4}$ mole-%, relative to the total epoxidation feed. When the only reaction modifier used in the epoxidation feed is an organic chloride, the organic chloride may be present in a quantity of at most $50 \times 10^{-4}$ mole-%, relative to the total epoxidation feed, in particular at most $20 \times 10^{-4}$ mole-%, more in particular at most $10 \times 10^{-4}$ mole-%, relative to the total epoxidation feed. When the only reaction modifier used in the epoxidation feed is an organic chloride, the organic chloride reaction modifier may be present in a quantity of at least $5 \times 10^{-5}$ mole-%, relative to the total epoxidation feed, in particular at least $7.5 \times 10^{-5}$ mole-%, more in particular at least $1 \times 10^{-4}$ mole-%, relative to the total epoxidation feed.

The epoxidation feed also contains a recycle gas. The epoxidation reaction product comprises the alkylene oxide, unreacted alkene, unreacted oxygen, and optionally, an organic chloride reaction modifier, a nitrogen-containing reaction modifier, a saturated hydrocarbon, an inert dilution gas, and other reaction by-products such as carbon dioxide and water. The reaction product is passed through one or more separation systems, such as an alkylene oxide absorber and a carbon dioxide absorber, so the unreacted alkene and oxygen as well as other components such as the dilution gases and reaction modifier may be recycled to the reactor system. The recycle gas loop comprises interconnecting pipework between the alkylene oxide absorber and the epoxidation reactor vessel and optionally includes a carbon dioxide absorber, heat exchangers, compressors, and water removal ("knock-out) vessels in the recycle gas loop. Carbon dioxide is a by-product in the epoxidation process. However, carbon dioxide generally has an adverse effect on the catalyst activity. Typically, a quantity of carbon dioxide in the epoxidation feed in excess of 25 mole-%, in particular in excess of 10 mole-%, relative to the total epoxidation feed, is avoided. A quantity of carbon dioxide of less than 3 mole-%, preferably less than 2 mole-%, more preferably less than 1 mole-%, relative to the total epoxidation feed, may be employed. Under commercial operations, a quantity of carbon dioxide of at least 0.1 mole-%, in particular at least 0.2 mole-%, relative to the total epoxidation feed, may be present in the epoxidation feed.

The epoxidation feed may also comprise a saturated hydrocarbon. The saturated hydrocarbon may be selected from methane, ethane, propane, butane, pentane, hexane, heptane, octane, nonane, decane, undecane, dodecane and mixtures thereof. In particular, the saturated hydrocarbon may be selected from methane, ethane, propane, and mixtures thereof, preferably methane. Saturated hydrocarbons are common dilution gases in an epoxidation process.

Saturated hydrocarbons, in particular methane, ethane and mixtures thereof, more in particular methane, may be present in a quantity of at most 80 mole-%, relative to the total epoxidation feed, in particular at most 75 mole-%, more in particular at most 65 mole-%, on the same basis. The saturated hydrocarbons may be present in a quantity of at least 1 mole-%, preferable at least 10 mole-%, more preferably at least 30 mole-%, most preferably at least 40 mole-%, on the same basis. Saturated hydrocarbons may be added to the epoxidation feed in order to increase the oxygen flammability limit.

Inert dilution gases, for example nitrogen, helium or argon, may be present in the epoxidation feed in a quantity of from 30 to 90 mole-%, typically from 40 to 80 mole-%, relative to the total epoxidation feed.

The epoxidation process is preferably carried out at a reactor inlet pressure in the range of from 1000 to 3500 kPa. "GHSV" or Gas Hourly Space Velocity is the unit volume of gas at normal temperature and pressure (0° C., 1 atm, i.e. 101.3 kPa) passing over one unit volume of packed catalyst per hour. Preferably, when the epoxidation process is a gas phase process involving a packed catalyst bed, the GHSV is in the range of from 1500 to 10000 Nl/(l·h). Preferably, the process is carried out at a work rate in the range of from 0.5 to 10 kmole alkylene oxide produced per $m^3$ of catalyst per hour, in particular 0.7 to 8 kmole alkylene oxide produced per $m^3$ of catalyst per hour, for example 5 kmole alkylene oxide produced per $m^3$ of catalyst per hour. As used herein, the work rate is the amount of the alkylene oxide produced per unit volume of catalyst per hour and the selectivity is the molar quantity of the alkylene oxide formed relative to the molar quantity of the alkene converted. As used herein, the activity is a measurement of the temperature required to achieve a particular ethylene oxide production level. The lower the temperature, the better the activity.

The epoxidation reaction product exiting the epoxidation reactor may contain contaminants such as acids, esters, aldehydes, acetals and organic halides. Contaminants may be removed from the epoxidation reaction product before it is supplied to the alkylene oxide absorber. A preferred method of removing contaminants is quenching, preferably by contacting the epoxidation reaction product with a cooled recirculating aqueous solution. Quenching is preferably carried out in the same vessel as the alkylene oxide absorber; the quench section is preferably below the vertically stacked trays or the packing of the alkylene oxide absorber. A portion of the recirculating aqueous solution may be withdrawn as a bleed stream from the quench section, and any alkylene oxide in the bleed stream may be recovered by conventional methods. After quenching, the epoxidation reaction product may be reheated before it is supplied to the alkylene oxide absorber, preferably by heat integration with the hot epoxidation reaction product from the epoxidation reactor.

The epoxidation reaction product is then supplied to an alkylene oxide absorber comprising a column of vertically stacked trays or comprising a packed column. The trays or the packed column provide a surface area for the lean absorbent and the epoxidation reaction product to come into contact, facilitating mass transfer between the two phases. Additionally, trays provide considerable liquid volume in which the liquid phase reaction can occur. In the embodiment wherein the alkylene oxide absorber comprises a series of vertically stacked trays, gases can pass upwards through the trays and liquid can flow downwards from tray to tray. Preferably the column comprises at least 20 trays, more preferably at least 30 trays. Preferably the column comprises less than 70 trays. More trays increase the absorption ability and reaction volume of the column, but adding additional trays increases expense. In the embodiment wherein the alkylene oxide absorber comprises a packed column, conventional packing such as structured packing, random packing and catalytic distillation internals may be used.

The epoxidation reaction product is preferably supplied at the bottom of the alkylene oxide absorber. If the alkylene oxide absorber comprises a column of vertically stacked trays, the epoxidation reaction product is preferably supplied below the bottom tray in the column. If the alkylene oxide absorber comprises a packed column, the epoxidation reaction product is preferably supplied below the packing material.

Lean absorbent is supplied to the alkylene oxide absorber and contacted with the epoxidation reaction product in the alkylene oxide absorber and fat absorbent (comprising components absorbed from the epoxidation reaction product including alkylene carbonate and/or alkylene glycol) is withdrawn from the alkylene oxide absorber. In one embodiment, the lean absorbent is supplied at the top of the alkylene oxide absorber. If the alkylene oxide absorber comprises a column of vertically stacked trays, the lean absorbent is preferably supplied to the uppermost tray in the absorption column. If the alkylene oxide absorber comprises a packed column, the lean absorbent is preferably supplied above the packing material. In another embodiment, the lean absorbent is supplied such that there are trays or packing above the point at which the lean absorbent is supplied to the alkylene oxide absorber. In this embodiment, cold water or additional lean absorbent that has been cooled can be supplied at the top of the alkylene oxide absorber to absorb alkylene oxide or contaminants in the top of the alkylene oxide absorber.

The lean absorbent comprises water. The lean absorbent may comprise at least 20 wt % water. The water that is present in the lean absorbent may be used in the hydrolysis of alkylene oxide and alkylene carbonate that may occur in the alkylene oxide absorber. If the lean absorbent comprises less than 20 wt % water, then less hydrolysis is likely to occur and the conversion to alkylene glycol may be lower. Also, depending on the nature of the one or more catalysts that promote carboxylation and hydrolysis, catalyst performance may suffer if the lean absorbent comprises less than 20 wt % water. Preferably, the lean absorbent comprises at least 30 wt % water, more preferably at least 40 wt % water. Preferably the lean absorbent comprises less than 80 wt % water. More than 80 wt % water in the lean absorbent may still provide good selectivity and catalyst performance, but higher quantities of water require additional water removal, with associated energy and equipment costs. The lean absorbent may also comprise alkylene glycol and alkylene carbonate.

The epoxidation reaction product is contacted with lean absorbent in the alkylene oxide absorber in the presence of an iodide-containing carboxylation catalyst and optionally a hydrolysis catalyst. If this occurs in the presence of two or more catalysts, then each catalyst can promote carboxylation or hydrolysis or can promote both reactions. In a preferred embodiment the epoxidation reaction product is contacted with lean absorbent in the presence of at least two catalysts including a first iodide-containing catalyst that promotes carboxylation and a second catalyst that promotes hydrolysis. The carboxylation and hydrolysis catalysts may be homogeneous and/or heterogeneous. When heterogeneous catalysts are used, the catalyst is contained in the vertically stacked trays or in the packing of a packed column.

The iodide-containing carboxylation catalyst may be a homogenous catalyst. Suitable homogenous iodide-containing catalysts that are known to promote carboxylation may include alkali metal iodides such as potassium iodide, and halogenated organic phosphonium or ammonium salts such as tributylmethylphosphonium iodide, tetrabutylphosphonium iodide, triphenylmethylphosphonium iodide, and tributylmethylammonium iodide.

The iodide-containing carboxylation catalyst may be a heterogeneous iodide-containing catalysts. Suitable heterogeneous iodide-containing catalysts that are known to promote carboxylation may include quaternary ammonium and quaternary phosphonium iodides immobilized on silica, quaternary ammonium and quaternary phosphonium iodides bound to insoluble polystyrene beads, and metal iodide salts such as zinc iodide immobilised on solid supports containing quaternary ammonium or quaternary phosphonium groups, such as ion exchange resins containing quaternary ammonium or quaternary phosphonium groups.

A homogeneous hydrolysis catalyst may be present in the alkylene oxide absorber. Suitable homogeneous hydrolysis catalysts may include basic alkali metal salts such as potassium carbonate, potassium hydroxide and potassium bicarbonate, or alkali metal metalates such as potassium molybdate.

A heterogeneous hydrolysis catalyst may be present in the alkylene oxide absorber. Suitable heterogeneous hydrolysis catalysts may include metalates immobilised on solid supports, for example molybdates, vanadates or tungstates immobilised on ion exchange resins containing quaternary ammonium or quaternary phosphonium groups, or basic anions such as bicarbonate ions immobilised on solid supports, for example bicarbonate immobilised on ion exchange resins containing quaternary ammonium or quaternary phosphonium groups.

Preferably, a combination catalyst system for carboxylation and hydrolysis are present in the alkylene oxide absorber and may include a combination of potassium iodide and potassium carbonate, or a combination of potassium iodide and potassium molybdate.

In the embodiment wherein the epoxidation reaction product is contacted with lean absorbent in the presence of at least two catalysts including a first iodide-containing catalyst that promotes carboxylation and a second catalyst that promotes hydrolysis, the ratio of first catalyst to second catalyst can be adjusted in order to vary the amount of carbon dioxide that is consumed or released in the alkylene oxide absorber. Preferably the recycle gases exiting from the alkylene oxide absorber are partially or entirely supplied to a carbon dioxide absorption column wherein the carbon dioxide is at least partially absorbed by a recirculating absorbent stream. By controlling the amount of carbon dioxide that is consumed or released in the alkylene oxide absorber, the capacity and cost of a carbon dioxide absorber column can be reduced.

It has been found that gaseous iodide-containing impurities may be formed which exit the alkylene oxide absorber with the recycle gas stream. The gaseous iodide-containing impurities generated may include inorganic iodide compounds and organic iodide compounds. Iodide-containing impurities such as these can poison the epoxidation catalyst in the epoxidation reactor. Contacting the recycle gas with a purification absorbent capable of reducing the quantity of iodide-containing impurities can reduce the quantity of iodide-containing impurities in the recycle gas and thus improve the performance of the epoxidation catalyst, in particular selectivity, activity, and the duration of time the epoxidation catalyst remains in the epoxidation reactor before having to exchange the catalyst with a fresh epoxidation catalyst.

The temperature in the alkylene oxide absorber is preferably from 50° C. to 160° C., preferably from 80° C. to 150° C. This is higher than the temperature in an absorber in a conventional process and is required to promote the carboxylation and hydrolysis reactions. Temperature higher than 160° C. is not preferred as this may reduce the selectivity of the alkylene oxide conversion to alkylene glycol. Both the epoxidation reaction product and the lean absorbent are preferably supplied to the alkylene oxide absorber at temperatures in the range from 50° C. to 160° C.

The pressure in the alkylene oxide absorber is from 1 to 4M Pa, preferably from 2 to 3 MPa. The preferred pressure is a compromise between lower pressures that require less expensive equipment (e.g. equipment having thinner walls) and higher pressures that increase absorption and reduce the volumetric flow of the gas, thereby reducing the size of equipment and piping.

At least 50% of the alkylene oxide entering the alkylene oxide absorber is converted in the alkylene oxide absorber. The alkylene oxide may undergo carboxylation, providing alkylene carbonate. The alkylene oxide may undergo hydrolysis, providing alkylene glycol. Additionally, the alkylene carbonate that is produced from the alkylene oxide may undergo hydrolysis, providing alkylene glycol. Preferably at least 60% of the alkylene oxide entering the alkylene oxide absorber is converted in the alkylene oxide absorber, more preferably at least 70%.

The epoxidation reaction product that is supplied to the alkylene oxide absorber comprises carbon dioxide. It is possible that the epoxidation reaction product may contain insufficient carbon dioxide to achieve desired levels of carboxylation. This is likely to be the case when using a freshly prepared epoxidation catalyst in the epoxidation reactor. An additional source of carbon dioxide is preferably supplied to the alkylene oxide absorber, e.g. recycle carbon dioxide from a finishing reactor, carbon dioxide from a carbon dioxide recovery unit or, at start-up, carbon dioxide from an external source. The ratio of the total amount of carbon dioxide supplied to the alkylene oxide absorber to the amount of alkylene oxide supplied to the alkylene oxide absorber is preferably between 5:1 and 1:3, more preferably between 3:1 and 4:5. A higher quantity of carbon dioxide improves the selectivity of the process because most alkylene oxide reacts with carbon dioxide to alkylene carbonate, which may be subsequently hydrolysed to alkylene glycol and there is less opportunity for reaction between alkylene oxide and alkylene glycol to produce higher glycols. However, a higher quantity of carbon dioxide also requires either additional removal capacity for carbon dioxide in the process, which can be costly, or operating the epoxidation catalyst at higher carbon dioxide concentration which adversely affects the epoxidation catalyst performance.

Gases that are not absorbed in the alkylene oxide absorber are preferably partially or entirely supplied to a carbon dioxide absorption column wherein the carbon dioxide is at least partially absorbed by a recirculating absorbent stream. Gases that are not absorbed by the recirculating absorbent stream are preferably recombined with any gases bypassing the carbon dioxide absorption column and are recycled to the epoxidation reactor. Preferably the gases are cooled prior to recycle to the epoxidation reactor in order to reduce the water content. This is preferred because the performance of the epoxidation catalyst in the epoxidation reactor may be detrimentally affected by an excess of water. The water removed from the recycle gas stream can optionally be recirculated to the alkylene oxide absorber.

Fat absorbent is withdrawn from the alkylene oxide absorber, preferably by withdrawing liquid from the bottom of the alkylene oxide absorber, i.e. below the vertically stacked trays or packing.

In one embodiment of the invention, a portion or all of the fat absorbent from the alkylene oxide absorber is supplied to one or more finishing reactors. Supply to one or more finishing reactors is preferred if a significant quantity (e.g. at least 1%) of alkylene oxide or alkylene carbonate is not converted to alkylene glycol in the alkylene oxide absorber. Hydrolysis catalyst may be supplied to one or more of the finishing reactors to convert the alkylene carbonate. Conversely, if the majority (e.g. greater than 90%) of alkylene oxide and alkylene carbonate is converted to alkylene glycol in the alkylene oxide absorber, then one or more finishing reactors may not be required and the equipment used in the process is thereby reduced. To maximise conversion of alkylene oxide in the alkylene oxide absorber, spraying nozzles can be employed in the sump (bottom section) of the alkylene oxide absorber, to disperse carbon dioxide and promote carboxylation.

Preferably, at least 90% of alkylene oxide and alkylene carbonate entering the one or more finishing reactors is converted to alkylene glycol in the one or more finishing reactors. This means that if there is one finishing reactor, at least 90% of alkylene oxide and alkylene carbonate entering the finishing reactor is converted to alkylene glycol in the finishing reactor, and if there is more than one finishing reactor, at least 90% of alkylene oxide and alkylene carbonate entering the first finishing reactor is converted to alkylene glycol before leaving the final finishing reactor. Preferably at least 95% of alkylene oxide and alkylene carbonate entering the one or more finishing reactors is converted to alkylene glycol in the one or more finishing reactors, more preferably at least 98%.

In an embodiment, all of the fat absorbent is supplied to at least one of the one or more finishing reactors in a finishing zone. In another embodiment, a portion of the fat absorbent is supplied to at least one of the one or more finishing reactors in a finishing zone. Preferably, 10-90 wt % of the fat absorbent is supplied to at least one of the one or more finishing reactors, most preferably 30-70 wt % is supplied to at least one of the one or more finishing reactors. Preferably, the portion of the fat absorbent that is supplied to at least one of the one or more finishing reactors is pre-heated prior to supply to at least one of the one or more finishing reactors. Preferably the portion of the fat absorbent is pre-heated to a temperature in the range 100-200° C., preferably about 150° C., in a heat exchanger.

If there is more than one finishing reactor it is preferred that the finishing reactors are connected in series, i.e. the fat absorbent must pass through each finishing reactor sequentially.

In an embodiment, at least one of the one or more finishing reactors is a baffled reactor, wherein the baffled reactor has at least four compartments, the compartments are formed by internal baffles and the internal baffles provide a sinuous route for reaction fluid through the reactor. Optionally steam is injected into the baffled reactor.

Carbon dioxide may be produced in the one or more finishing reactors and is preferably separated from the product stream as it leaves the one or more finishing reactors and recycled.

The temperature in the one or more finishing reactors is typically from 100 to 200° C., preferably from 100 to 180° C. The pressure in the one or more finishing reactors is typically from 0.1 to 3 MPa.

The fat absorbent from the alkylene oxide absorber or a product stream from at least one of the one or more finishing reactors is optionally supplied to a flash vessel wherein light ends are removed. The flash vessel may be located directly after the alkylene oxide absorber so the fat absorbent passes directly to the flash vessel. When there is at least one finishing reactor, the flash vessel may be located after all of the one or more finishing reactors so that the product stream passes to the flash vessel. When there is more than one finishing reactor, the flash vessel may be located between the finishing reactors such that the fat absorbent from the alkylene oxide absorber passes to at least one finishing reactor, then the product stream passes to the flash vessel and then the stream from the flash vessel passes to at least another finishing reactor.

The light ends are preferably recirculated to the alkylene oxide absorber; they may be combined with the epoxidation reaction product before it is supplied to the alkylene oxide absorber, or the light ends may be supplied at the bottom of the alkylene oxide absorber. Recirculating the light ends to the alkylene oxide absorber increases the efficiency of the process because light ends, comprising alkene, are recovered and are not lost when carbon dioxide is removed from the process in a carbon dioxide bleed stream.

The flash can be at pressure from 0.01 to 2 MPa, preferably from 0.1 to 1 MPa, most preferably from 0.1 to 0.5 MPa.

Fat absorbent from the alkylene oxide absorber or flash vessel, or the product stream from the one or more finishing reactors or flash vessel is supplied to a dehydrator in a dehydration zone. The stream that is supplied to the dehydrator preferably comprises very little alkylene oxide or alkylene carbonate, i.e. most of the alkylene oxide or alkylene carbonate has been converted to alkylene glycol prior to supply to the dehydrator column, either in the alkylene oxide absorber or in a finishing reactor. Preferably the molar ratio of alkylene glycol to alkylene oxide and alkylene carbonate (combined) in the stream supplied to the dehydrator column is greater than 90:10, more preferably greater than 95:5, most preferably greater than 99:1.

The dehydrator is preferably one or more columns, including at least one vacuum column, preferably operating at a pressure of less than 0.05 MPa, more preferably less than 0.025 MPa and most preferably about 0.0125 MPa.

The dehydrated product stream is purified in a alkylene glycol purification zone to remove impurities and provide a purified alkylene glycol product stream. The alkylene glycol purification zone contains one or more purification columns. If one or more of the carboxylation and/or hydrolysis catalysts are homogeneous catalysts, it will be necessary to separate the one or more catalysts from the dehydrated product stream, preferably in a flash vessel. The one or more homogeneous catalysts are preferably recombined with the lean absorbent and supplied to the alkylene oxide absorber.

FIG. 1 shows a preferred embodiment of the process of the invention. Ethylene, oxygen, methane and reaction modifier (e.g. ethyl chloride) are supplied to the recycle gas at (1). A purification zone (45) containing an absorbent capable of reducing the quantity of iodide-containing impurities is located in the recycle gas loop downstream from the addition of ethylene, oxygen, methane and reaction modifier and upstream from the product/feed heat exchanger. In the ethylene epoxidation reactor (2), the ethylene and oxygen react in the presence of an epoxidation catalyst positioned within a plurality of reactor tubes of a shell-and-tube reactor, providing an epoxidation reaction product containing ethylene, oxygen, methane, ethylene oxide, organic chloride reaction modifier, carbon dioxide, and by-products, which is cooled and supplied to the quench (4), below the bottom tray of the quench section. The quenched gas is reheated and fed to the ethylene oxide absorber column (3) below the bottom tray or below the packing material. Optionally, additional carbon dioxide from the carbon dioxide recovery section (7)

or second finishing reactor (14) may also be supplied to the ethylene oxide absorber (3) or may be mixed with the gases before supply to the ethylene oxide absorber. Lean absorbent comprising at least 20 wt % water, a homogeneous hydrolysis catalyst and a homogeneous iodide-containing carboxylation catalyst is supplied (5) at the top of the ethylene oxide absorber (3). In the ethylene oxide absorber, ethylene oxide and carbon dioxide are absorbed into the lean absorbent and react to provide ethylene carbonate. The ethylene carbonate and ethylene oxide react with water to provide ethylene glycol. The gases that are not absorbed in the ethylene oxide absorber (3) are partially or entirely supplied to carbon dioxide recovery section (7) where carbon dioxide is removed from the gas. The recovered carbon dioxide stream (8) can partially or entirely be recirculated to the ethylene oxide absorber (3), directly or by mixing with the epoxidation reaction product gas feed. The gas from the ethylene oxide absorber column (3), the gas from carbon dioxide recovery section (7) and the recombined gas stream fed to the reactor can be cooled to reduce the water content. The liquid knocked out of the gas stream can optionally be recirculated to the ethylene oxide absorber column (3). Fat absorbent is withdrawn (6) from the ethylene oxide absorber bottom and is supplied to a flash vessel (9) where light ends are removed. The light ends stream (10) can be recirculated to the ethylene oxide absorber (3) directly or by mixing with the epoxidation reaction product gas feed. The fat absorbent stream is split and one portion is fed to heat exchanger (12) and is subsequently supplied to a finishing reactor (13). In the finishing reactor (13), further reaction of ethylene carbonate to ethylene glycol and ethylene oxide to ethylene glycol occurs. The carbon dioxide gas released (14) can be recycled to the ethylene oxide absorber (3) directly, or by mixing with the epoxidation reaction product gas feed, or can be totally or partially bled. The liquid product stream from the finishing reactor (13) is supplied to a dehydrator (15) where water is removed. The dehydrated product stream is withdrawn from the dehydrator (15) and supplied to the monoethylene glycol (MEG) purification column (16). A solution comprising the iodide-containing carboxylation catalyst and hydrolysis catalyst dissolved in glycols (17) is withdrawn from the bottom of the MEG purification column (16) and is recycled to the ethylene oxide absorber (3) as lean absorbent (5) after mixing with the absorbent flow that is not supplied to the finishing reactor (11). Monoethylene glycol product (18) is withdrawn from the MEG purification column top section. Make-up water (19) can be supplied to the lean absorbent.

Figure 2:
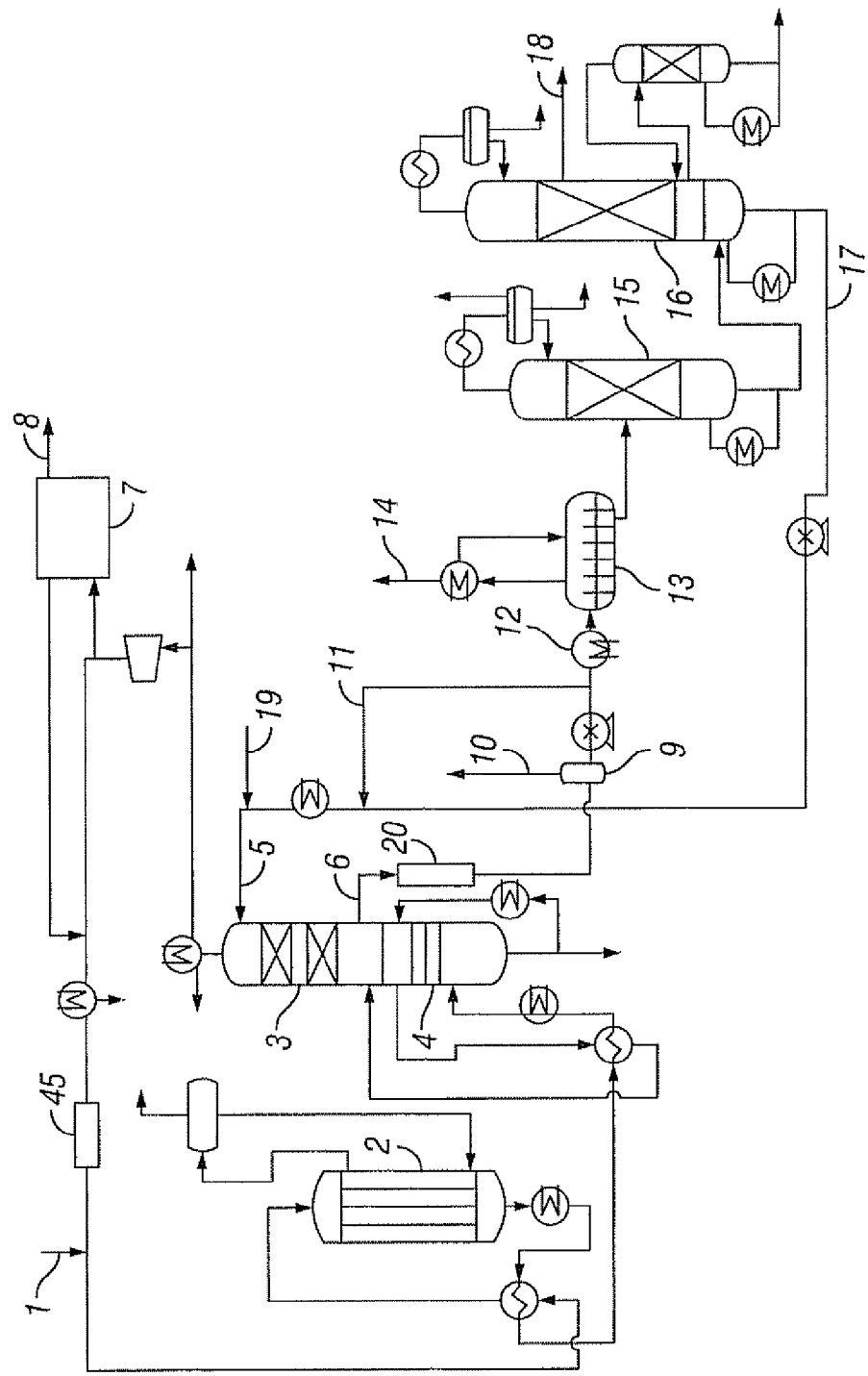
FIG. 2 is a schematic diagram showing a process according to another embodiment of the invention.

FIG. 2 shows an alternative preferred embodiment of the process of the invention where the fat absorbent stream (6) from the ethylene oxide absorber column (3) is supplied directly to a first finishing reactor (20) to convert all remaining ethylene oxide to ethylene carbonate and/or ethylene glycol before supply to the flash vessel (9). As in FIG. 1, after the flash vessel the stream is split and one portion is fed to heat exchanger (12) and is subsequently supplied to a finishing reactor (13) wherein further reaction of ethylene carbonate to ethylene glycol and ethylene oxide to ethylene glycol occurs. In FIG. 2, the finishing reactor (13) is the second finishing reactor. In FIG. 2, the purification zone (45) is located in the recycle gas loop downstream from the carbon dioxide recovery section (7) and upstream from the addition of ethylene, oxygen, methane and reaction modifier.

Figure 3:
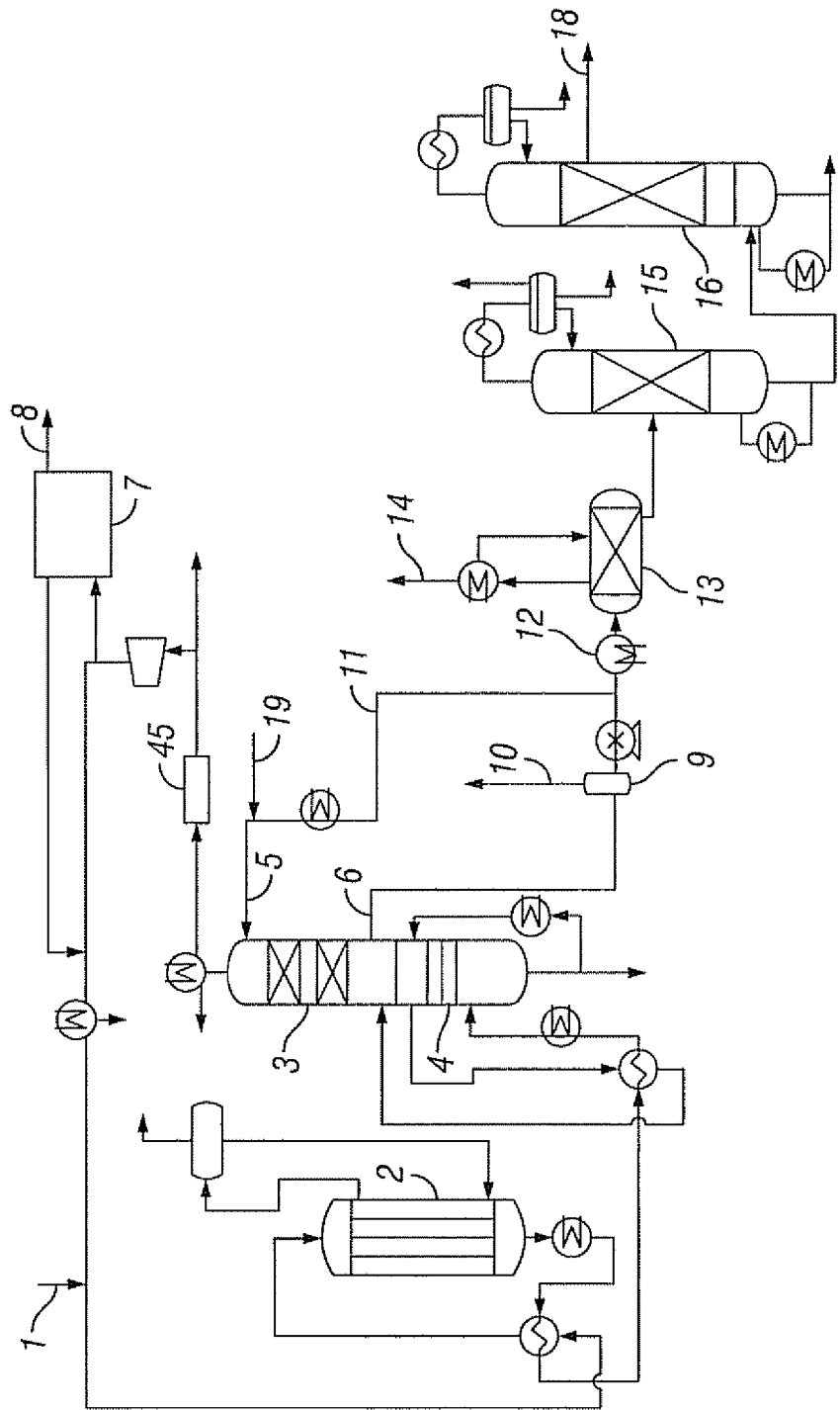
FIG. 3 is a schematic diagram showing a process according to another embodiment of the invention.

FIG. 3 shows yet another preferred embodiment of the process comprising a heterogeneous catalyst packing in the ethylene oxide absorber column (3) as well as a heterogeneous catalyst bed in the finishing reactor (13). In this embodiment there is no catalyst recirculation flow needed from the bottom of MEG purification column (17). In FIG. 3, the purification zone (45) is located in the recycle gas loop between the ethylene oxide absorber column (3) and the carbon dioxide recovery section (7).

Figure 4:
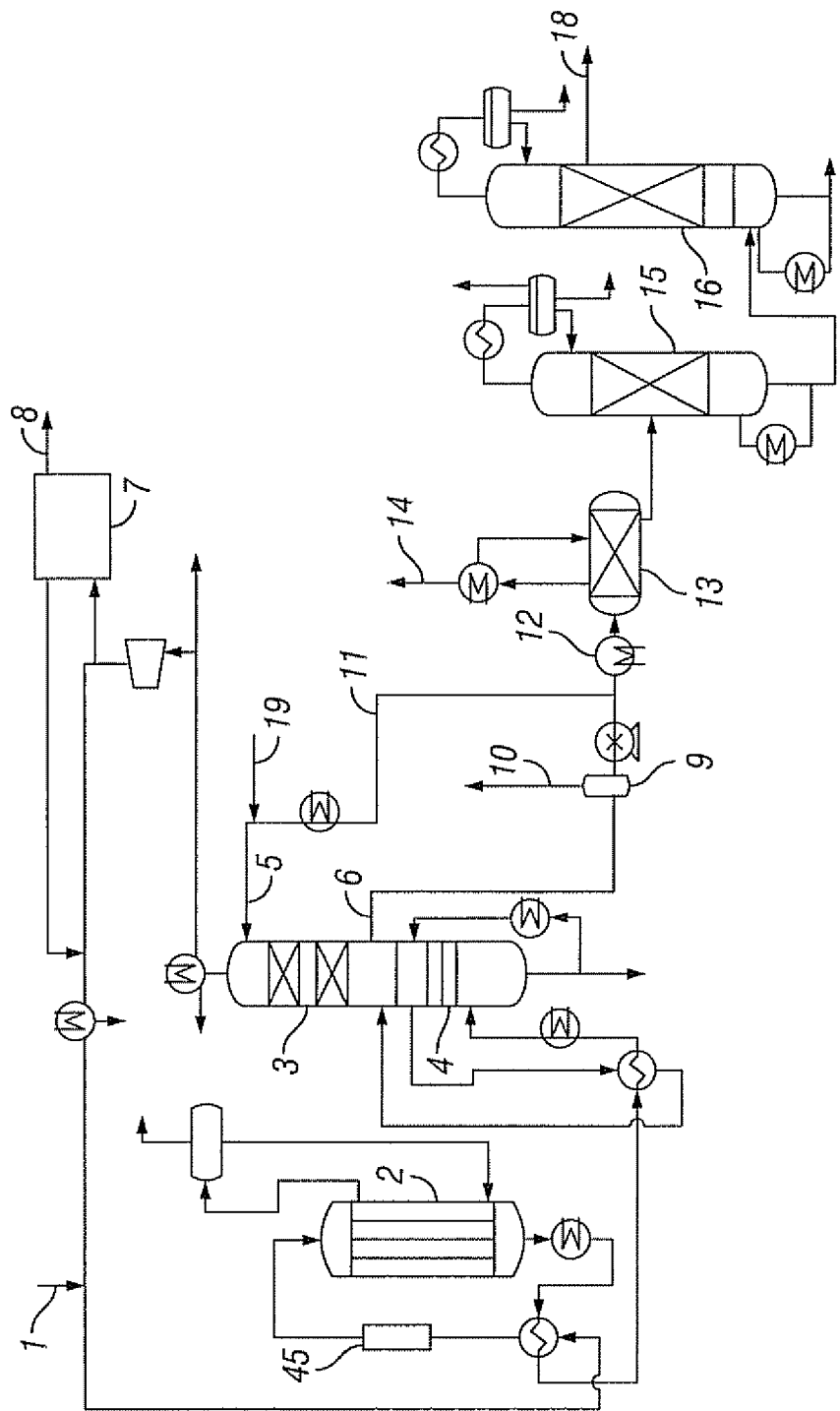
FIG. 4 is a schematic diagram showing a process according to another embodiment of the invention.

FIG. 4 shows an embodiment where packing or trays are present in ethylene oxide absorber column (3) above the point where lean absorbent enters the column. Cold water or absorbent can be fed to the column above this top packing or top trays to absorb remaining ethylene oxide and/or contaminants in the top of the ethylene oxide absorber. In FIG. 4, the purification zone (45) is located in the recycle gas loop between the product/feed heat exchanger and the inlet of the ethylene epoxidation reactor (2).

Figure 5:
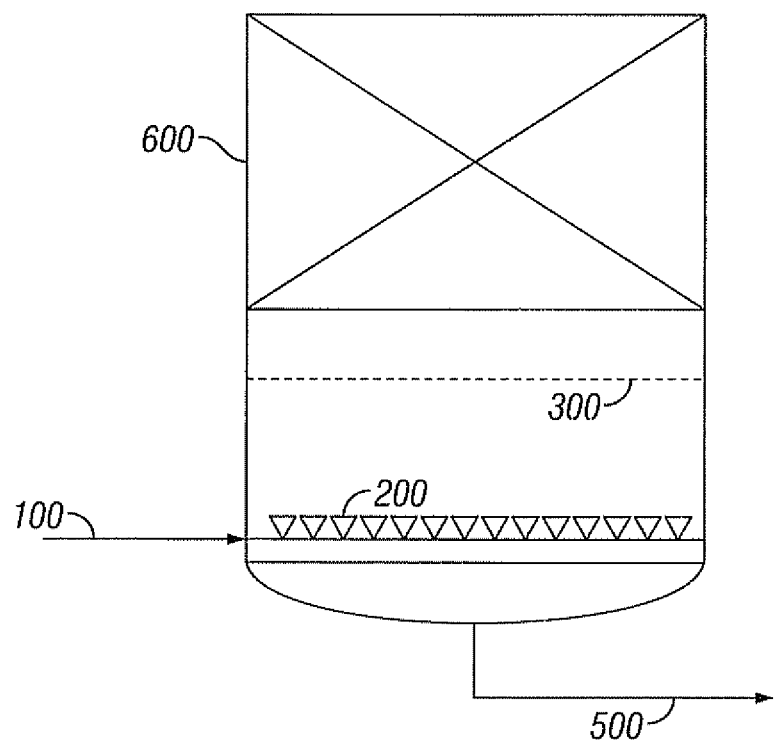
FIG. 5 is a schematic diagram showing an embodiment of the bottom or sump of the alkylene oxide absorber column.

FIG. 5 describes an embodiment of the bottom or sump of the ethylene oxide absorber column, where carbon dioxide gas (100) is supplied to the liquid though nozzles (200). The liquid level (300) is maintained well below the bottom tray or below the bottom of the column packing (600). Fat absorbent (500) leaves at the bottom.

Figure 6:
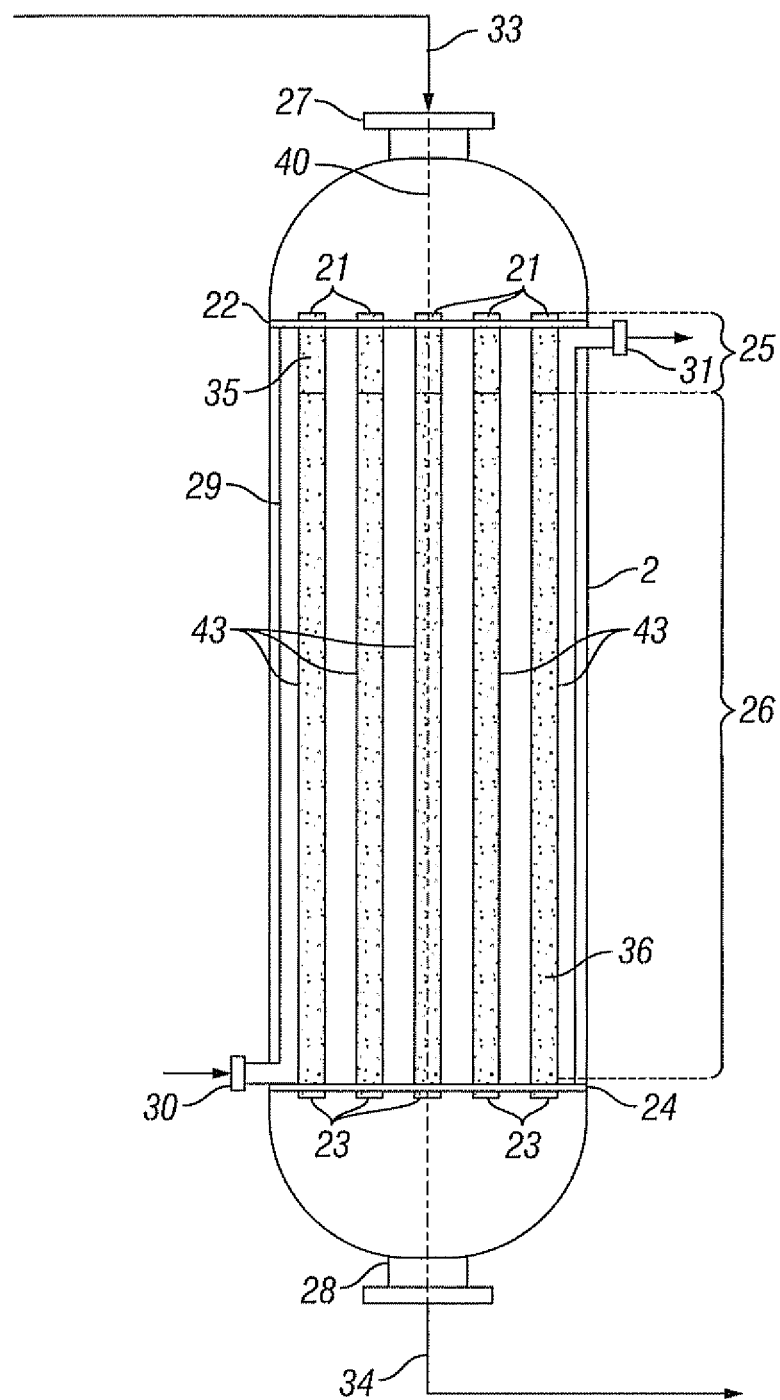
FIG. 6 is a schematic diagram showing an embodiment where the purification zone is located in the epoxidation reactor vessel within the epoxidation reactor tubes upstream from the epoxidation zone.

FIG. 6 describes an embodiment where the purification zone is located within the epoxidation reactor tubes. The epoxidation reactor (2) comprises a shell-and-tube heat exchanger reactor vessel having a substantially vertical vessel and a plurality of open-ended reactor tubes (43) positioned substantially parallel to the central longitudinal axis (40) of the epoxidation reactor vessel (2). The upper ends (21) of the reactor tubes (43) are connected to a substantially horizontal upper tube plate (22) and the lower ends (23) of the reactor tubes (43) are connected to a substantially horizontal lower tube plate (24). The upper tube plate (22) and the lower tube plate (24) are supported by the inner wall of the reactor vessel (2). The plurality of reactor tubes (43) contain a purification zone (25) and an epoxidation zone (26) positioned downstream from the purification zone (25). The purification zone (25) contains a purification absorbent (35). The epoxidation zone (26) contains an epoxidation catalyst (36). The epoxidation zone (26) is supported in the reactor tubes (43) by a catalyst support means (not shown) arranged in the lower ends (23) of the reactor tubes (43). Components of the feed (33), such as the alkene, oxygen and recycle gas, enter the reactor vessel (2) via one or more inlets such as inlet (27) which are in fluid communication with the upper ends (21) of the reactor tubes (43). The epoxidation reaction product (34) exits the epoxidation reactor vessel (2) via one or more outlets such as outlet (28) which are in fluid communication with the lower ends (23) of the reactor tubes (43). The heat exchange fluid enters the heat exchange chamber (29) via one or more inlets such as inlet (30) and exits via one or more outlets such as outlet (31). The heat exchange chamber (29) may be provided with baffles (not shown) to guide the heat exchange fluid through the heat exchange chamber (29).

Figure 7:
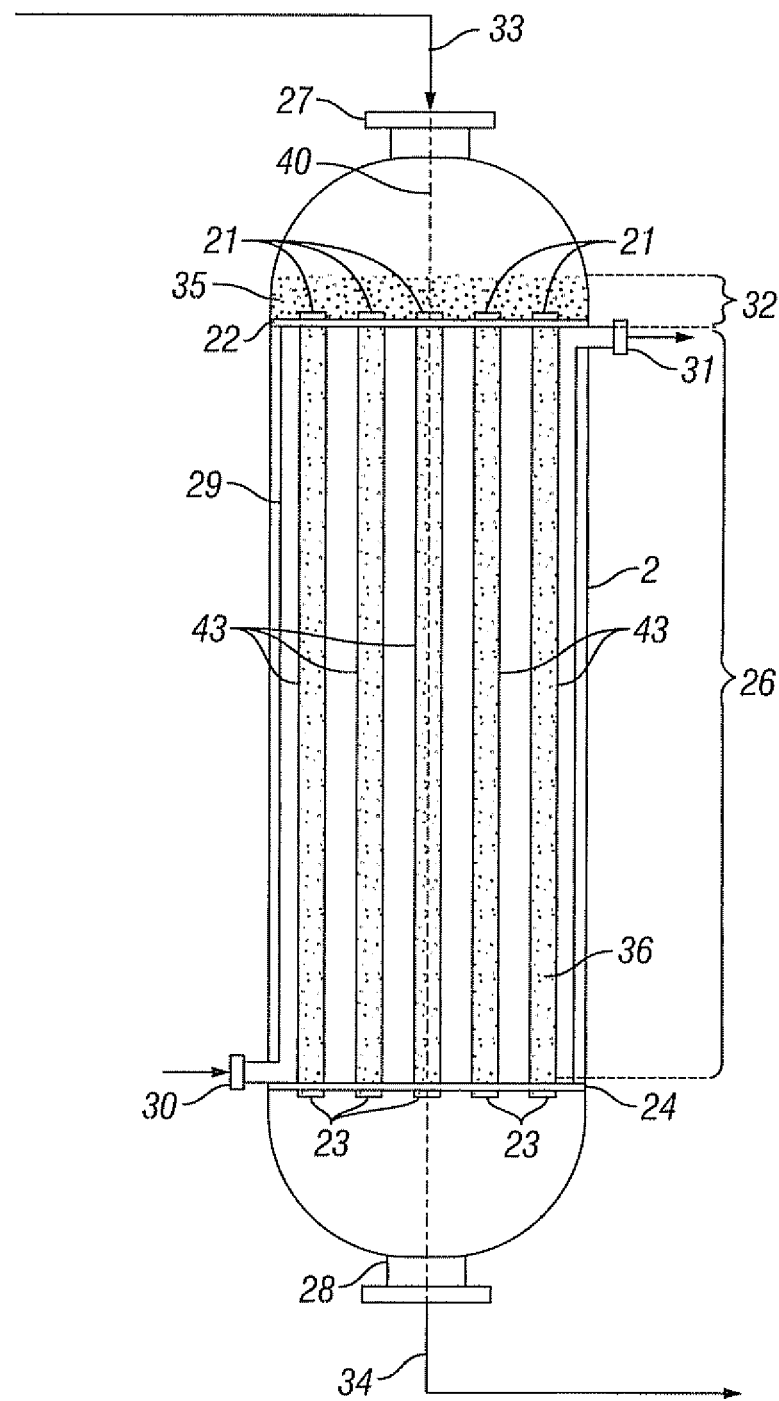
FIG. 7 is a schematic diagram showing an embodiment where the purification zone is located in the epoxidation reactor vessel upstream from the reactor tubes and the epoxidation zone.

FIG. 7 is a schematic view of an epoxidation reactor (2) similar to FIG. 6 except that the purification zone (32) is positioned upstream from the reactor tubes (43).

Example 1

An investigation of potential iodide guard bed materials was undertaken with the following characteristics in mind. To serve as a practical guard bed, a material must 1) quantitatively capture sub-ppm-level iodides, while operating at conditions that are consistent with the process of the present invention; 2) operate efficiently even at very high space velocities, since high guard bed space velocity equates to a relatively small (and affordable) guard bed size relative to the catalyst bed size; and 3) display thermal stability and complete inertness toward the feedstock components themselves.

A 16-microtube enhanced experimentation reactor was used to rapidly assess the effectiveness of a number of candidates to sorb organic iodide using actual process gas matrix, process temperature and pressure conditions. Both silver-based and silver-free materials that quantitatively sorb ethyl iodide in such a process at 170° C. were identified.

Catalyst Preparation

A variety of formulations were tested for guard bed effectiveness. Some candidates were prepared on low surface area alpha-alumina (~1 m²/g) and/or high surface area gamma-alumina (~120 m²/g) without transition metals, utilizing as sorbants only the neutral or basic salts lithium hydroxide, sodium hydroxide, potassium carbonate, potassium nitrate, or calcium acetate. Some candidates contained transition metals, and were prepared using water-soluble salts of tungsten, molybdenum, iron, manganese, cobalt, tin, zinc, aluminum, chromium, zirconium, lead, copper, nickel, and silver were loaded onto low surface area alpha-alumina. Since the data clearly showed silver to be the most iodine sorbing material, some silver formulations were also prepared on high surface area gamma-alumina. For silver based materials, the formulations included enough sodium (as either chloride or nitrate) or potassium (as nitrate) to effectively deactivate the silver with respect to olefin oxidation capability. Also, some of the silver based materials were calcined prior to use, in an attempt to redistribute the impregnated salts in order to provide more small pore access to the gas stream. Silver can be suitably deposited on support material as silver salts, complexes, oxides, hydroxide, sols, metallic silver.

Method 1

Materials identified as Prep Method 1 were unadulterated aluminas, used without any modifications.

Method 2

Aqueous solutions, generally using as much salt as would easily dissolve in the water, were used to vacuum impregnate carrier. The vacuum was broken and the material was allowed to stand for 3 minutes. The material was centrifuged for 2 minutes at 200 rpm. The centrifuged material was then dried in a stream of flowing air in a vibrating perforated basket at 170° C. for 2 minutes.

Method 3

Carrier was vacuum impregnated with concentrated aqueous silver nitrate. Pellets were drained and gently rolled on paper towel that had been moistened with deionized water. The pellets were then placed into a beaker of aqueous alkali salt to allow the intrusion of alkali ions into the pores of the carrier. Pellets were again drained and rolled on moistened paper towel. The drained pellets were centrifuged for 2 minutes at 200 rpm. The centrifuged material was then dried in a stream of flowing air in a vibrating perforated basket at 170° C. for 2 minutes.

Method 4

Alkali salt was included in the same solution as the silver nitrate, and introduced in a single impregnation. The pellets were centrifuged for 2 minutes at 200 rpm. The centrifuged material was then dried in a stream of flowing air in a vibrating perforated basket at 170° C. for 2 minutes.

Method 5

Preparation was the same as Method 4, but was then followed by a calcination in flowing air at 250° C. for 15 minutes.

Method 6

An aqueous solution containing silver oxalate, ethylene diamine, potassium nitrate, ammonium tungstate, and lithium hydroxide was used to prepare catalyst 118. Due to the lower solubility of the silver oxalate based formulation, two sequential impregnations were used, with a 7 minute, 250° C. drying step in flowing air following each impregnation. The levels of silver, tungsten, potassium and lithium on the final material were 27% w, 0.008% w, 0.1% w, and 0.009% w, respectively.

Catalyst Evaluation

The objectives of these experiments were to 1) rank order potential guard bed candidates, and 2) provide a semi-quantitative estimate of the useful sorption capacity of the candidates. The testing conditions and feed stream that were utilized are summarized in the top section of Table 1. A temperature of 170° C. was used as representative of the typical process temperature immediately upstream of the EO reactor inlet head. Methyl iodide and ethyl iodide, which were chosen as the representative organic iodides for this experiment, were introduced at levels ranging from 2 ppmv to 48.

The iodide content of inlet and outlet streams was measured using a VG Prima dB process mass spectrometer (MS) manufactured by ThermoFisher Scientific. The mass spectrometer was configured to identify methyl and ethyl iodides. The instrument was calibrated over the range of 0.1-10 ppmv iodide (i.e., the concentration region where we were most interested in obtaining highly precise measurements that would indicate the onset of iodide breakthrough) using a custom blend that contained 10.5 ppm of each compound, with balance nitrogen. The mass spectrometer was found to provide reliable measurements of relative iodide concentrations in the outlet of reactor.

TABLE 1

Summary of Testing Conditions
Feedstock Constitution & Process Conditions

| | | | |
|---|---|---|---|
| Avg. Rx Flow (Nml/min) | 7.0 | Guard Bed Mass (g) | 0.060 |
| $C_2H_4$ (%) | 35.0 | GHSV basis guard bed ($hr^{-1}$) | 5200 |
| $O_2$ (%) | 7.5 | P(psig/barg) | 210/14.7 |
| $CO_2$ (%) | 0.6 | Temp (° C.) | 170 |
| Vinyl Chloride (ppm) | 2.0 | Methyl or Ethyl Iodide (ppm) | 2, 4, 28, 48 |

GHSV = gas hourly space velocity

The constraints of the system imposed one deviation from the conditions for a pilot- or industrial-size guard bed. It is likely that a substrate loading of 0.06 g is the smallest bed for which good gas contact can be assured. The highest practical reactor flowrate in the reactors used herein is about 7 cc/min. This combination of bed size and flowrate corresponds to a space velocity of about 5200 $hr^{-1}$ if one makes the preliminary approximation that guard bed materials will have roughly the same packing density. We believe that a practical industrial-size guard bed mass would need to contain no more than about 10% of the catalyst bed mass. For example, with an epoxidation process employing a space velocity of 3,400 $hr^{-1}$, we would expect a space velocity with respect to the guard bed of 34,000 $hr^{-1}$. Since the current study was a screening study intended to rank-order candidate guard bed materials, this hardware limitation is not regarded as problematic.

Iodide-free feedstock was at first fed to all reactor tubes to equilibrate temperatures and feed composition. Then methyl iodide or ethyl iodide was introduced into the gas stream. The outlet gas of each tube was sequentially analyzed for iodide content and the analytical cycle was continually repeated. Tube #1 was left empty to allow confirming analysis of the feed stream during each cycle. The data are most usefully expressed as "percent iodide breakthrough", or "% BT". For example, when 2.1 ppmv iodide is fed to a candidate guard bed and 0.21 ppmv iodide is detected at the outlet of the guard bed, a "% BT" value of 10% is reported for that time interval. In some experiments, the iodide concentration fed to the beds was progressively increased from 2.1 ppmv to 4.2, 28, and 48 ppmv. In other experiments involving silver-based materials, where we had already established the ability of the material to effectively sorb iodides, we immediately began flowing 48 ppmv iodide.

We had previously established that the performance of ethylene oxide catalysts is extremely sensitivity toward organic iodides. Therefore, the guard bed that protects the catalyst from volatile iodides in the process must provide virtually quantitative blocking of iodides. This means that in practice a guard bed must be recharged at the point where % BT is very low. The data from our tests are summarized in tabular form in Table 2. The terminology in Table 2 shows two different types of "percent" parameter. "% BT"=the percent iodide breakthrough as compared with the level of iodide in the feed stream. In some cases, % BT was immediately 100%, meaning that the candidate material was utterly ineffective for iodide capture. In other cases, the candidate material was indeed initially effective at iodide capture. As such an experiment continues and progressively more iodide has been sorbed by the candidate material, the ability of the material to sorb iodide eventually begins to deteriorate. The data in the body of Table 2 are the sorption capacities (in units of "mass elemental iodine sorbed per mass of guard bed material") that have been exhibited at the times when 10%, 25% or 50% of the feed stream iodide is 'breaking through' the bed. For each experiment, the percent sorption capacity at each level of breakthrough (10% BT, 25% BT and 50% BT) was equal to the cumulative amount of iodine that was actually sorbed during each sorption interval.

As an example, for each candidate guard bed material, the column "@10% BT" displays the amount of iodine (elemental iodine sorbed expressed as a weight-percent of the guard bed mass) that had been fed to the bed when we first observed 10% iodine breakthrough. For example, in the last line of data in Table 2, we see that candidate 118-1 had sorbed iodine equivalent to 15% of the bed mass (or in absolute terms, 0.15*0.060=0.0090 g elemental iodine) at the moment when "10% breakthrough" was initially observed. The material continued to sorb iodine, but with decreasing efficiency, until at the point of "25% breakthrough", candidate 118-1 had sorbed iodine equivalent to 23% of the bed mass (or in absolute terms, 0.23*0.060=0.0138 g elemental iodine). At the point of "50% breakthrough", when the bed's effectiveness had deteriorated to the point that only half of the organic iodide in the feed stream was intercepted, candidate 118-1 had sorbed iodine equivalent to 28% of the bed mass (or in absolute terms, 0.28*0.060=0.0168 g elemental iodine).

Guard bed candidates that did not contain silver performed very poorly and did not sorb measurable amounts of iodine. Silver-based candidates all exhibited both highly efficient iodide capture (i.e., we observed absolutely no iodine in the outlet stream for an extended period of time), and impressive absolute sorption capacities. We see in Table 2 that some of the candidate guard beds were still 90% effective for sorbing iodine after the bed had sorbed on the order of 15-25% w iodine basis guard bed mass. As a practical example, a 1 kg guard bed 134-1 will remain 90% effective for sorbing iodine (i.e., will continue to operate below 10% breakthrough) even after it has sorbed an amount of organic iodide corresponding to 0.25 kg iodine.

For many of the comparisons, we observed no clear trend with respect to the high surface area alumina candidates versus the low surface area alumina candidates. However, the very best results at the 10% BT blocking level were achieved for with $KNO_3$ and $NaNO_3$ alkaline earth salts and high SA (see 134-1,2,3,4 near the bottom). We thus believe that the High SA is better than the Low SA carrier. Other high surface area supports such as silica should also work. Sorption data for methyl iodide were similar to corresponding data for ethyl iodide in all cases where we tested both.

TABLE 2

Effectiveness of Candidate Guard Bed Materials for Blocking Methyl or Ethyl Iodide.

| Guard Bed | Transition Metal | Soluble Metal Salt Used | Loading (% w metal) | Added Alkali or Alkaline Earth Salt | (% w as oxide)[2] | Carrier | [1]Prep Method | Methyl or Ethyl Iodide | SORPTION CAPACITY[4], i.e., Cumulative Iodide Fed, at Several "% BT" Values, Expressed as "% w Iodine Basis Guard Bed Mass" | | |
|---|---|---|---|---|---|---|---|---|---|---|---|
| | | | | | | | | | @10% BT | @25% BT | @50% BT |
| 016-1 | none | none | none | none | | Alumina (High S.A.) | 1 | Me | <1% | <1% | <1% |
| 016-1 | none | none | none | none | | Alumina (High S.A.) | 1 | Et | <1% | <1% | <1% |
| 016-2 | none | none | none | none | | Alumina (Low S.A.) | 1 | Me | <1% | <1% | <1% |
| 016-2 | none | none | none | none | | Alumina (Low S.A.) | 1 | Et | <1% | <1% | <1% |
| 143-3 | none | none | none | none | | $CaCO_3$ tech grade | 1 | Et | <1% | <1% | <1% |
| 143-1 | none | none | none | none | | $CaCO_3$ reagent grade | 1 | Et | <1% | <1% | <1% |
| 143-2 | none | none | none | none | | Kaolinite Clay | 1 | Et | <1% | <1% | <1% |
| 126-2 | none | none | none | NaOH | 19% | Alumina (High S.A.) | 2 | Me | <1% | <1% | <1% |
| 126-3 | none | none | none | LiOH | 9% | Alumina (High S.A.) | 2 | Me | <1% | <1% | <1% |
| 119-2 | none | none | none | $K_2CO_3$ | 17% | Alumina (Low S.A.) | 2 | Et | <1% | <1% | <1% |
| 128-1 | none | none | none | $KNO_3$ | 19% | Alumina (High S.A.) | 2 | Me | <1% | <1% | <1% |
| 128-2 | none | none | none | $KNO_3$ | 13% | Alumina (Low S.A.) | 2 | Me | <1% | <1% | <1% |
| 120-1 | none | none | none | CaOAc | 9% | Alumina (High S.A.) | 2 | Et | <1% | <1% | <1% |
| 120-2 | none | none | none | CaOAc | 6% | Alumina (Low S.A.) | 2 | Me | <1% | <1% | <1% |
| 120-2 | none | none | none | CaOAc | 6% | Alumina (Low S.A.) | 2 | Et | <1% | <1% | <1% |
| 137-1 | W | Ammonium Metatungstate | 68% | none | | Alumina (Low S.A.) | 2 | Me | <1% | <1% | <1% |

TABLE 2-continued

Effectiveness of Candidate Guard Bed Materials for Blocking Methyl or Ethyl Iodide.

| Guard Bed | Metal | Soluble Metal Salt Used | Transition Metal Loading (% w metal) | Added Alkali or Alkaline Earth Salt | (% w as oxide)[2] | Carrier | [1]Prep Method | Methyl or Ethyl Iodide | SORPTION CAPACITY[4], i.e., Cumulative Iodide Fed, at Several "% BT" Values, Expressed as "% w Iodine Basis Guard Bed Mass" | | |
|---|---|---|---|---|---|---|---|---|---|---|---|
| | | | | | | | | | @10% BT | @25% BT | @50% BT |
| 137-2 | Mo | Ammonium Heptamolybdate Tetrahydrate | 20% | none | — | Alumina (Low S.A.) | 2 | Me | <1% | <1% | <1% |
| 137-3 | Fe | Iron(III) Nitrate Nonahydrate | 33% | none | — | Alumina (Low S.A.) | 2 | Me | <1% | <1% | <1% |
| 139-1 | Mn | Manganese(II) Nitrate Hydrate | 11% | none | — | Alumina (Low S.A.) | 2 | Me | <1% | <1% | <1% |
| 139-3 | Co | Cobalt(II) Nitrate Hexahydrate | 8% | none | — | Alumina (Low S.A.) | 2 | Me | <1% | <1% | <1% |
| 140-1 | Sn | Tin(II) Chloride Dihydrate | 20% | none | — | Alumina (Low S.A.) | 2 | Me | <1% | <1% | <1% |
| 140-2 | Zn | Zinc(II) Sulfate Monohydrate | 14% | none | — | Alumina (Low S.A.) | 2 | Me | <1% | <1% | <1% |
| 140-3 | Al | Aluminum(III) Nitrate Nonahydrate | 3% | none | — | Alumina (Low S.A.) | 2 | Me | <1% | <1% | <1% |
| 141-1 | Cr | Chromium(III) Nitrate Nonahydrate | 9% | none | — | Alumina (Low S.A.) | 2 | Me | <1% | <1% | <1% |
| 141-2 | Zr | Zyrconyl(IV) Nitrate Hydrate | 8% | none | — | Alumina (Low S.A.) | 2 | Me | <1% | <1% | <1% |
| 141-3 | Pb | Lead(II) Nitrate | 24% | none | — | Alumina (Low S.A.) | 2 | Me | <1% | <1% | <1% |
| 142-1 | Cu | Copper(II) Nitrate Hemi Pentahydrate | 11% | none | — | Alumina (Low S.A.) | 2 | Me | <1% | <1% | <1% |
| 142-2 | Ni | Nickel(II) Nitrate Hexahydrate | 17% | none | — | Alumina (Low S.A.) | 2 | Me | <1% | <1% | <1% |
| 116-1 | Ag | Silver Nitrate | 24% | NaCl | n.a.[3] | Alumina (High S.A.) | 3 | Et | 7% | 8% | 30% |
| 116-2 | Ag | Silver Nitrate | 17% | NaCl | n.a.[3] | Alumina (Low S.A.) | 3 | Et | 10% | 10% | 11% |
| 117-1 | Ag | Silver Nitrate | 24% | NaOH | n.a.[3] | Alumina (High S.A.) | 3 | Me | 10% | 10% | 12% |
| 117-1 | Ag | Silver Nitrate | 24% | NaOH | n.a.[3] | Alumina (High S.A.) | 3 | Et | 9% | 11% | 13% |
| 117-2 | Ag | Silver Nitrate | 17% | NaOH | n.a.[3] | Alumina (Low S.A.) | 3 | Me | 16% | 17% | 17% |
| 117-2 | Ag | Silver Nitrate | 17% | NaOH | n.a.[3] | Alumina (Low S.A.) | 3 | Et | 13% | 13% | 13% |
| 127-1 | Ag | Silver Nitrate | 24% | $KNO_3$ | 6% | Alumina (High S.A.) | 4 | Me | 13% | 14% | 19% |
| 127-2 | Ag | Silver Nitrate | 17% | $KNO_3$ | 6% | Alumina (Low S.A.) | 4 | Me | 16% | 16% | 16% |
| 134-1 | Ag | Silver Nitrate; Calcined | 17% | $KNO_3$ | 6% | Alumina (High S.A.) | 5 | Me | 25% | 26% | 26% |
| 134-2 | Ag | Silver Nitrate; Calcined | 24% | $KNO_3$ | 6% | Alumina (Low S.A.) | 5 | Me | 16% | 16% | 16% |
| 134-3 | Ag | Silver Nitrate; Calcined | 17% | $NaNO_3$ | 6% | Alumina (High S.A.) | 5 | Me | 24% | 25% | 25% |
| 134-4 | Ag | Silver Nitrate; Calcined | 24% | $NaNO_3$ | 6% | Alumina (Low S.A.) | 5 | Me | 12% | 12% | 13% |
| 118-1 | Ag | Sivler Oxalate | 27% | $KNO_3$ | 0.10% | Alumina (Low S.A.) | 6 | Me | 15% | 23% | 28% |

Testing conditions are provided in Table 1.
[1]Preparation methods are described in the text.
[2]% w is defined basis finished doped material.
[3]Salt added by diffusion (see text); precise salt levels were not quantified.
[4]"10% BT" = point when 10% of iodide feed passes uncaptured through candidate guard bed.

The invention claimed is:

1. A reaction system for producing an alkylene carbonate and/or an alkylene glycol comprising:
  a recycle gas loop fluidly connected to a source of alkene and oxygen, the recycle gas loop comprising an inlet and an outlet;
  an epoxidation reactor comprising an epoxidation catalyst, an inlet, and an outlet, wherein the outlet of the recycle gas loop is fluidly connected to the inlet of the epoxidation reactor;
  an alkylene oxide absorber comprising an iodide-containing carboxylation catalyst, an inlet, and an outlet,
    wherein the outlet of the epoxidation reactor is fluidly connected to the inlet of the alkylene oxide absorber,
    wherein the outlet of the alkylene oxide absorber is fluidly connected to the inlet of the recycle gas loop, and
    wherein the alkylene oxide absorber is configured to produce an epoxidation recycle gas comprising iodide-containing impurities at the outlet; and
  a purification vessel located in the recycle gas loop, the purification vessel comprising a purification absorbent that comprises silver, an alkali or alkaline earth metal component, and a support material having a surface area of more than 20 $m^2/g$,
    wherein the purification vessel is configured to reduce a quantity of iodide-containing impurities in at least a portion of the epoxidation recycle gas.

2. The reaction system of claim 1 wherein the epoxidation reactor is a shell-and-tube heat exchanger comprising a plurality of reactor tubes positioned substantially parallel to the central longitudinal axis of the epoxidation reactor;
wherein upper ends of the reactor tubes are connected to a substantially horizontal upper tube plate and lower ends of the reactor tubes are connected to a substantially horizontal lower tube plate; and
wherein the epoxidation catalyst is in the form of a packed bed positioned within the reactor tubes.

3. The reaction system of claim 1 wherein the purification absorbent is present in a packed bed and is configured to withstand a temperature in the range of from 25 to 325° C.

4. The reaction system of claim 1 wherein the alkylene oxide absorber further comprises a hydrolysis catalyst.

5. The reaction system of claim 1 further comprising:
a finishing reactor fluidly connected to the alkylene oxide absorber.

6. The reaction system of claim 5 further comprising:
a dehydrator fluidly connected to the finishing reactor.

7. The reaction system of claim 6 further comprising:
an alkylene glycol purification column fluidly connected to the dehydrator.

8. The reaction system of claim 1 further comprising:
a dehydrator fluidly connected to the alkylene oxide absorber.

9. The reaction system of claim 8 further comprising:
an alkylene glycol purification column fluidly connected to the dehydrator.

10. The reaction system of claim 1 further comprising a carbon dioxide absorber located in the recycle gas loop.

11. The reaction system of claim 10 wherein the purification vessel located in the recycle gas loop is positioned between the outlet of the alkylene oxide absorber and an inlet of the carbon dioxide absorber.

12. The reaction system of claim 1 further comprising a heat exchanger located in the recycle gas loop.

13. The reaction system of claim 12 wherein the purification vessel located in the recycle gas loop is positioned between the heat exchanger and the inlet of the epoxidation reactor.

14. The reaction system of claim 1 further comprising a water removal vessel located in the recycle gas loop.

* * * * *